(12) United States Patent
Hueffer et al.

(10) Patent No.: US 11,512,268 B2
(45) Date of Patent: Nov. 29, 2022

(54) STORAGE-STABLE ENZYME PREPARATIONS, THEIR PRODUCTION AND USE

(71) Applicant: BASF SE, Ludwigshafen am Rhein (DE)

(72) Inventors: Stephan Hueffer, Ludwigshafen (DE); Alejandra Garcia Marcos, Ludwigshafen (DE); Oliver Spangenberg, Ludwigshafen (DE); Matthias Kellermeier, Ludwigshafen (DE); Susanne Wolwertz, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 159 days.

(21) Appl. No.: 16/768,109

(22) PCT Filed: Nov. 19, 2018

(86) PCT No.: PCT/EP2018/081707
§ 371 (c)(1),
(2) Date: May 29, 2020

(87) PCT Pub. No.: WO2019/105781
PCT Pub. Date: Jun. 6, 2019

(65) Prior Publication Data
US 2020/0291334 A1 Sep. 17, 2020

(30) Foreign Application Priority Data

Nov. 29, 2017 (EP) .................................. 17204357.2
Nov. 29, 2017 (EP) .................................. 17204358.0

(51) Int. Cl.
| | | |
|---|---|---|
| C11D 3/386 | (2006.01) | |
| C11D 3/20 | (2006.01) | |
| C11D 11/00 | (2006.01) | |
| C07C 219/06 | (2006.01) | |
| C12N 9/14 | (2006.01) | |
| C12N 9/96 | (2006.01) | |
| C11D 3/30 | (2006.01) | |
| C11D 3/37 | (2006.01) | |

(52) U.S. Cl.
CPC ........ *C11D 3/38663* (2013.01); *C07C 219/06* (2013.01); *C11D 3/20* (2013.01); *C11D 3/30* (2013.01); *C11D 3/3707* (2013.01); *C11D 3/38618* (2013.01); *C11D 3/38627* (2013.01); *C11D 3/38636* (2013.01); *C11D 11/0017* (2013.01); *C12N 9/14* (2013.01); *C12N 9/96* (2013.01)

(58) Field of Classification Search
CPC ............ C11D 3/38663; C11D 11/0017; C07C 219/06
See application file for complete search history.

(56) References Cited

U.S. PATENT DOCUMENTS

| | | | | |
|---|---|---|---|---|
| 3,896,034 A * | 7/1975 | Eckert | .................... | C11D 3/001 510/516 |
| 4,187,184 A * | 2/1980 | Becker | ................. | C11D 3/3715 510/517 |
| 6,008,178 A * | 12/1999 | Baillely | ................. | C11D 3/386 510/351 |
| 2005/0197270 A1* | 9/2005 | Kaasgaard | ........... | C11D 3/0084 510/392 |

(Continued)

FOREIGN PATENT DOCUMENTS

| | | |
|---|---|---|
| CN | 1396267 A | 2/2003 |
| EP | 0478050 A1 | 4/1992 |

(Continued)

OTHER PUBLICATIONS

STIC Search. Dec. 2020. (Year: 2020).*

(Continued)

*Primary Examiner* — Liam J Heincer
*Assistant Examiner* — M. Reza Asdjodi
(74) *Attorney, Agent, or Firm* — Armstrong Teasdale LLP

(57) ABSTRACT

Described herein is a liquid enzyme preparation containing component (a): at least one salt according to general formula (I)

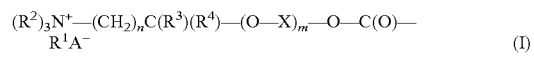

wherein
n is selected from 1 to 12,
m is selected from zero to 50,
$R^1$ is selected from the group consisting of methyl, ethyl, —CH(OH)—CH(OH)—COOH, CH(OH)—CH$_3$, (E)-CH=CHCOOH, (Z)—CH=CHCOOH, —C$_6$H$_5$, para-HO—C$_6$H$_4$—, o,p-dihydroxyphenyl, and 3,4,5-triydroxyphenyl,
$R^2$ are same or different and selected from C$_1$-C$_{10}$-alkyl, phenyl,
$R^3$ and $R^4$ are same or different and selected from hydrogen and C$_1$-C$_4$-alkyl,
X is C$_2$-C$_4$-alkylen, and
$A^-$ is an inorganic or organic counteranion,
component (b): at least one enzyme selected from hydrolases (EC 3),
and
optionally component (c): at least one compound selected from enzyme stabilizers different from component (a), preservatives, and surfactants.

20 Claims, No Drawings

(56) References Cited

U.S. PATENT DOCUMENTS

| | | | |
|---|---|---|---|
| 2006/0127974 A1* | 6/2006 | Kaasgaard | C12N 1/38 |
| | | | 435/69.1 |
| 2009/0317515 A1* | 12/2009 | Lohscheidt | A23K 20/189 |
| | | | 435/187 |
| 2011/0301071 A1* | 12/2011 | Nielsen | C11D 3/245 |
| | | | 510/218 |
| 2017/0037043 A1* | 2/2017 | Liu | C07D 455/03 |
| 2019/0177665 A1* | 6/2019 | Spangenberg | C11D 3/33 |
| 2019/0292494 A1* | 9/2019 | Jenewein | C11D 3/166 |
| 2020/0291334 A1* | 9/2020 | Hueffer | C11D 3/38636 |
| 2021/0071118 A1* | 3/2021 | Hueffer | C11D 3/38663 |

FOREIGN PATENT DOCUMENTS

| | | | | |
|---|---|---|---|---|
| EP | 0634485 A1 * | 1/1995 | | C11D 3/3942 |
| EP | 0634485 A1 * | 1/1995 | | |
| EP | 0709449 A1 * | 1/1996 | | |
| EP | 0709449 A1 | 5/1996 | | |
| GB | 2008641 A | 6/1979 | | |
| WO | 9533033 A1 | 12/1995 | | |
| WO | WO-9533033 A1 * | 12/1995 | | C11D 1/65 |
| WO | 2014055936 A1 | 4/2014 | | |

OTHER PUBLICATIONS

Bisht, et al., "Influence of cholinium-based ionic liquids on the structural stability and activity of α-chymotrypsin", New Journal of Chemistry, vol. 41, Issue 22, 2017, pp. 13902-13911.

European Search Report for EP Patent Application No. 17204357.2, dated Nov. 16, 2018, 3 pages.

European Search Report for EP Patent Application No. 17204358.0, dated Apr. 6, 2018, 3 pages.

Xue, et al., "Choline acetate enhanced the catalytic performance of Candida rogusa lipase in AOT reverse micelles", Colloids and Surfaces B: Biointerfaces, vol. 105, May 1, 2013, pp. 81-86.

International Search Report and Written Opinion for corresponding PCT/EP2018/081707 dated Dec. 19, 2018, 9 pages.

* cited by examiner

STORAGE-STABLE ENZYME PREPARATIONS, THEIR PRODUCTION AND USE

CROSS-REFERENCE TO RELATED APPLICATIONS

This application is a U.S. National Phase Application of PCT/EP2018/081707, filed Nov. 19, 2018, which claims the benefit of priority to European Patent Application No. 17204357.2, filed Nov. 29, 2017, and which claims the benefit of priority to European Patent Application No. 17204358.0, filed Nov. 29, 2017 the entire contents of which are hereby incorporated by reference herein.

The present invention is directed towards an enzyme preparation containing
component (a): at least one salt according to general formula (I)

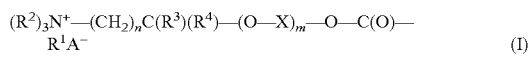

(I)

wherein
n is selected from 1 to 12,
m is selected from zero to 50,
$R^1$ is selected from $C_1$-$C_{10}$-alkyl, linear or branched, and $C_6$-$C_{10}$-aryl, wherein
$R^1$ may bear one or more hydroxyl or C=O or COOH groups, partially or fully neutralized, if applicable,
$R^2$ are same or different and selected from $C_1$-$C_{10}$-alkyl, phenyl,
$R^3$ and $R^4$ are same or different and selected from hydrogen and $C_1$-$C_4$-alkyl,
X is $C_2$-$C_4$-alkylen, and
$A^-$ is an inorganic or organic counteranion,
component (b): at least one enzyme selected from hydrolases (EC 3), and
optionally component (c): at least one compound selected from enzyme stabilizers different from component (a) and surfactants.

Enzymes are usually produced commercially as a liquid concentrate, frequently derived from a fermentation broth. The enzyme tends to be destabilized if it remains in an aqueous environment and so it is conventional practice to convert it to an anhydrous form: aqueous concentrates may be lyophilized or spray-dried e.g. in the presence of a carrier material to form aggregates. Usually, solid enzyme products need to be "dissolved" prior to use. To stabilize enzymes in liquid products enzyme inhibitors are known to be employed, preferably reversible enzyme inhibitors, to inhibit enzyme activity temporarily until the enzyme inhibitor is released.

Boric acid and boronic acids are known to reversibly inhibit proteolytic enzymes. A discussion of the inhibition of one serine protease, subtilisin, by boronic acid is provided in Molecular & Cellular Biochemistry 51, 1983, pp. 5-32. For reactivation, this inhibitor needs to be removed prior or during application, which can be done for example by dilution.

Furthermore, the stability of lipolytic enzymes is known to be improved by addition of a stabilising material such as boronic acid derivatives by reversibly forming a complex with the active site of the lipolytic enzyme (e.g. EP0478050).

Because of environmental considerations there is a demand for at least reducing the amounts of boron-containing compounds used for enzyme stabilization. There is a seek for alternatives to be used as enzyme stabilizers in the presence of enzymes.

The problem to be solved for the current invention relates to providing an alternative enzyme stabilizer. It was a further objective of the present invention to provide an enzyme preparation that allows to be flexibly formulated into formulations with either high or low water content, both with excellent shelf life with respect to the enzyme(s) contained therein.

The problem was solved by using at least one salt according to general formula (I) as an enzyme stabilizer, wherein the general formula (I) is as follows:

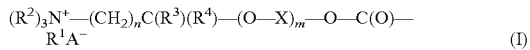

(I)

wherein,
n is selected from 1 to 12,
m is selected from zero to 50,
$R^1$ is selected from $C_1$-$C_{10}$-alkyl, linear or branched, and $C_6$-$C_{10}$-aryl, wherein $R^1$ may bear one or more hydroxyl or C=O or COOH groups, partially or fully neutralized, if applicable,
$R^2$ are same or different and selected from $C_1$-$C_{10}$-alkyl, phenyl,
$R^3$ and $R^4$ are same or different and selected from hydrogen and $C_1$-$C_4$-alkyl,
X is $C_2$-$C_4$-alkylen, and
$A^-$ is an inorganic or organic counteranion.

The enzyme stabilizer of the invention preferably stabilizes an enzyme selected from the group of hydrolases (EC 3). Enzyme names are known to those skilled in the art based on the recommendations of the Nomenclature Committee of the International Union of Biochemistry and Molecular Biology (IUBMB). Enzyme names include: an EC (Enzyme Commission) number, recommended name, alternative names (if any), catalytic activity, and other factors; see http://www.sbcs.qmul.ac.uk/iubmb/enzyme/EC3/ in the version last updated on 12 Mar. 2017.

In one embodiment, at least one hydrolase is selected from the group of enzymes acting on ester bond (EC 3.1), glycosylases (EC 3.2), and peptidases (EC 3.4).

The invention provides a liquid enzyme preparation containing
component (a): at least one salt according to general formula (I)

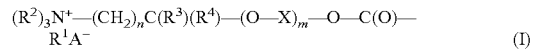

(I)

wherein
n is selected from 1 to 12,
m is selected from zero to 50,
$R^1$ is selected from $C_1$-$C_{10}$-alkyl, linear or branched, and $C_6$-$C_{10}$-aryl, wherein $R^1$ may bear one or more hydroxyl or C=O or COOH groups, partially or fully neutralized, if applicable,
$R^2$ are same or different and selected from $C_1$-$C_{10}$-alkyl, phenyl,
$R^3$ and $R^4$ are same or different and selected from hydrogen and $C_1$-$C_4$-alkyl,
X is $C_2$-$C_4$-alkylen, and
$A^-$ is an inorganic or organic counteranion,
component (b): at least one enzyme, preferably selected from hydrolases (EC 3), and
optionally component (c): at least one compound selected from enzyme stabilizers different from component (a) and surfactants.

The enzyme preparation of the invention may be liquid at 20° C. and 101.3 kPa. In one embodiment, liquid means that the enzyme preparation does not show traces of precipitate formation or turbidity even after 20 days of storage.

Component (a)

Salt (component (a)) is a salt of an organic ester of choline or of a derivative of choline. The anion of salt (component (a))—the counterion—may be inorganic or organic, organic being preferred. Examples of inorganic counterions of salt (component (a)) are nitrate, hydroxide, sulphate, phosphate, hydrogenphosphate, dihydrogenphosphate, carbonate, bicarbonate, and halide, for example bromide or chloride. Preferred are halide, especially chloride, and sulphate, carbonate, and bicarbonate. Examples of organic counterions are lactate, acetate, tartrate, citrate, and $CH_3SO_3^-$ (methanesulfonate). In embodiments with divalent or trivalent counterions, the respective molar amounts cation is present.

The nitrogen atom in salt (component (a)) bears three methyl groups and a hydroxyethyl group. The term derivatives of choline as used in the context of the present invention refers to compounds that bear at least one alkyl group other than a methyl group, or a hydroxyalkyl group other than a 2-hydroxyethyl group, or further alkoxy groups.

More specifically, component (a) is a compound of general formula (I)

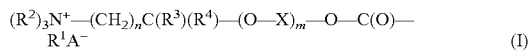

$$(R^2)_3N^+ \text{—} (CH_2)_nC(R^3)(R^4) \text{—} (O\text{—}X)_m \text{—} O\text{—}C(O)\text{—}R^1 A^- \qquad (I)$$

wherein, n is selected from 1 to 12, for example 1 to 9, preferably 1, 2, 3, or 4, and even more preferably n is 1;

m is selected from zero to 50, for example 2 to 50, preferred is 10 to 25. Most preferably, however, m is zero;

$R^1$ is selected from $C_1$-$C_{10}$-alkyl, linear or branched, and $C_6$-$C_{10}$-aryl, wherein $R^1$ may bear one or more hydroxyl or C=O or COOH groups, partially or fully neutralized, if applicable. Preferred examples of $R^1$ are non-substituted $C_1$-$C_6$-alkyl such as methyl, ethyl, n-propyl, isopropyl, n-butyl, iso-butyl, n-hexyl, preferred non-substituted $C_1$-$C_{10}$-alkyl are methyl and ethyl, furthermore substituted such $C_1$-$C_{10}$-alkyl as —CH(OH)—CH(OH)—COOH, CH(OH)—CH$_3$, (E)-CH=CHCOOH, (Z)—CH=CHCOOH, —C$_6$H$_5$, para-HO—C$_6$H$_4$—, o,p-dihydroxyphenyl, and 3,4,5-triydroxyphenyl. In a preferred embodiment, O—C(O)—R$^1$ together constitute a citrate. Even more preferred, $R^1$ is methyl;

$R^2$ are same or different and selected from phenyl and $C_1$-$C_{10}$-alkyl, for example methyl, ethyl, n-propyl, isopropyl, n-butyl, iso-butyl, sec.-butyl, tert.-butyl, n-pentyl, iso-pentyl, sec.-pentyl, neo-pentyl, 1,2-dimethylpropyl, iso-amyl, n-hexyl, iso-hexyl, sec.-hexyl, n-heptyl, n-octyl, 2-ethylhexyl, n-nonyl, n-decyl, 2-n-propyl-heptyl, or iso-decyl, preferred are linear $C_1$-$C_{10}$-alkyl and more preferred are linear $C_1$-$C_4$-alkyl, even more preferred at least two $R^2$ groups are CH$_3$ and the third $R^2$ is selected from linear $C_1$-$C_{10}$-alkyl, and most preferred, all $R^2$ are the same and methyl;

$R^3$ and $R^4$ are same or different and selected from hydrogen and $C_1$-$C_4$-alkyl, preferred are n—for example methyl, ethyl, n-propyl, and n-butyl, and even more preferred both $R^3$ and $R^4$ are hydrogen. In another embodiment, $R^3$ is $C_1$-$C_4$-alkyl and $R^4$ is hydrogen, preferably $R^3$ is methyl and $R^4$ is hydrogen;

X is $C_2$-$C_4$-alkylen, for example —CH$_2$—CH$_2$—, —CH(CH$_3$)—CH$_2$—, —(CH$_2$)$_3$—, CH$_2$—CH(CH$_3$)—, or —(CH$_2$)$_4$—; and $A^-$ is a counteranion, inorganic or organic. Examples of inorganic counterions of salt (component (a)) are sulphate, phosphate, hydrogenphosphate, dihydrogenphosphate, carbonate, bicarbonate, and halide, for example bromide or chloride. Preferred are halide, especially chloride, and sulphate, carbonate, and bicarbonate. Examples of organic counterions are lactate, acetate, tartrate, citrate, and $CH_3SO_3^-$ (methanesulfonate).

Component (a) is not a surfactant. In one embodiment, a solution of 5 g component (a) in 1000 g water has a dynamic surface tension of >45 mN/m at 20° C. and 101.3 kPa. A solution of 5 g component (a) in 1000 g water may have a dynamic surface tension of ≥50 mN/m at 20° C. and 101.3 kPa.

The dynamic surface tension may be measured with a bubble pressure tensiometer, wherein the maximum internal pressure of a gas bubble which is formed in a liquid by means of a capillary is measured; the measured value usually corresponds to the surface tension at a certain surface age, the time from the start of the bubble formation to the occurrence of the pressure maximum. In one embodiment, the surface age during measuring the dynamic surface tension at 20° C. and 101.3 kPa with a bubble pressure tensiometer is 50 ms.

Most preferred example of salts (component (a)) are salts of choline esters with tartrate or citrate as counterion, and salts of acetyl choline, choline citrate, and of choline tartrate, for example lactates, acetates, tartrates, citrates.

In embodiments wherein counteranion $A^-$ is—or may be—divalent such as sulphate, tartrate, carbonate, or polyvalent such as phosphate or citrate, the necessary positive charge may be furnished by another salt (component (a)) derived cation, or by alkali metal cations such as potassium or preferably sodium, or by ammonium, non-substituted or substituted with $C_1$-$C_4$-alkyl and/or with 2-hydroxyethyl.

In embodiments wherein $R^1$ bears one or more carboxyl groups they may be free COOH groups or partially or fully neutralized with alkali, for example potassium or especially sodium, or they may be esterified, for example with $(R^2)_3N^+$—$(CH_2)_n$—$(O$—$X)_m$—OH. Such embodiments result in the di- or triester, if applicable, of the respective di- or tricarboxylic acid. Mixtures of mono- and diesters of, e.g., tartaric acid or citric acid, and mixtures of di- and triesters of citric acid are feasible as well.

In a preferred embodiment of the present invention, salt (component (a)) is a compound according to formula (II)

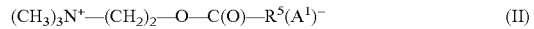

$$(CH_3)_3N^+ \text{—} (CH_2)_2 \text{—} O \text{—} C(O) \text{—} R^5 (A^1)^- \qquad (II)$$

wherein $(A^1)^-$ is selected from methanesulfonate, tartrate and citrate and wherein $R^5$ is selected from —CH$_2$—C(OH)(COOX$^2$)—CH$_2$—COOX$^2$ and —CH(OH)—CH(OH)—COOX$^1$ wherein X$^1$ is selected from hydrogen, alkali metal—especially sodium—and $(CH_3)_3N^+$—$(CH_2)_2$— and wherein X$^2$ are same or different and selected from hydrogen, alkali metal—especially sodium—and $(CH_3)_3N^+$—$(CH_2)_2$—. In a preferred embodiment, the ester group of O—C(O)—R$^5$ and (A$^1$)$^-$ correspond to each other.

In one embodiment of the present invention, liquid enzyme preparations contain component (a) in amounts in the range of 0.1% to 30% by weight, relative to the total weight of the enzyme preparation. The enzyme preparation may contain component (a) in amounts in the range of 0.1% to 15% by weight, 0.25% to 10% by weight, 0.5% to 10% by weight, 0.5% to 6% by weight, or 1% to 3% by weight, all relative to the total weight of the enzyme preparation.

In one embodiment of the present invention, salt (component (a)) contains as an impurity a compound (a') which is as follows:

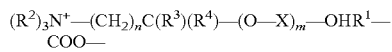

wherein the variables $R^1$, $R^2$, X, n and m are the same as in the corresponding salt (component (a)). Said impurity may amount to up to 50 mole-%, preferably 0.1 to 20 mole-%, even more preferably 1 to 10 mole-% of salt (component (a)). Although impurity compound (a') may stem from the synthesis of salt (component (a)) and may be removed by purification methods it is not preferred to remove it.

Component (b)

In one aspect of the invention, at least one enzyme comprised in component (b) is part of a liquid enzyme concentrate. "Liquid enzyme concentrate" herein means any liquid enzyme-comprising product comprising at least one enzyme. "Liquid" in the context of enzyme concentrate is related to the physical appearance at 20° C. and 101.3 kPa.

The liquid enzyme concentrate may result from dissolution of solid enzyme in solvent. The solvent may be selected from water and an organic solvent. A liquid enzyme concentrate resulting from dissolution of solid enzyme in solvent may comprise amounts of enzyme up to the saturation concentration.

Dissolution herein means, that solid compounds are liquified by contact with at least one solvent. Dissolution means complete dissolution of a solid compound until the saturation concentration is achieved in a specified solvent, wherein no phase-separation occurs.

In one aspect of the invention, component (b) of the resulting enzyme concentrate may be free of water, meaning that no significant amounts of water are present. Non-significant amounts of water herein means, that the enzyme preparation comprises less than 25%, less than 20%, less than 15%, less than 10%, less than 7%, less than 5%, less than 4%, less than 3%, less than 2% by weight water, all relative to the total weight of the enzyme concentrate, or no water.

In one embodiment, the enzyme preparation of the invention comprises at least one organic solvent selected from ethanol, n-propanol, iso-propanol, n-butanol, iso-butanol, sec.-butanol, ethylene glycol, propylene glycol, 1,3-propane diol, butane diol, glycerol, diglycol, propyl diglycol, butyl diglycol, hexylene glycol, ethylene glycol methyl ether, ethylene glycol ethyl ether, ethylene glycol propyl ether, and phenoxyethanol, preferred are ethanol, isopropanol or propylene glycol. Further, the enzyme preparation of the invention may comprise at least one organic solvent selected from compounds such as 2-butoxyethanol, isopropyl alcohol, and d-limonene.

Liquid enzyme concentrates comprising water may be called "aqueous enzyme concentrates". Aqueous enzyme concentrates may be enzyme-comprising solutions, wherein solid enzyme product has been dissolved in water. In one embodiment "aqueous enzyme concentrate" means enzyme-comprising products resulting from enzyme production by fermentation.

Fermentation means the process of cultivating recombinant cells which express the desired enzyme in a suitable nutrient medium allowing the recombinant host cells to grow (this process may be called fermentation) and express the desired protein. At the end of the fermentation, fermentation broth usually is collected and further processed, wherein the fermentation broth comprises a liquid fraction and a solid fraction. Depending on whether the enzyme has been secreted into the liquid fraction or not, the desired protein or enzyme may be recovered from the liquid fraction of the fermentation broth or from cell lysates. Recovery of the desired enzyme uses methods known to those skilled in the art. Suitable methods for recovery of proteins or enzymes from fermentation broth include but are not limited to collection, centrifugation, filtration, extraction, and precipitation.

Liquid enzyme concentrates, may comprise amounts of enzyme in the range of 0.1% to 40% by weight, or 0.5% to 30% by weight, or 1% to 25% by weight, or 3% to 25% by weight, or 5% to 25% by weight, all relative to the total weight of the enzyme concentrate. In one embodiment, liquid enzyme concentrates are resulting from fermentation and are aqueous.

Aqueous enzyme concentrates resulting from fermentation may comprise water in amounts of more than about 50% by weight, more than about 60% by weight, more than about 70% by weight, or more than about 80% by weight, all relative to the total weight of the enzyme concentrate. Aqueous enzyme concentrates which result from fermentation, may comprise residual components such as salts originating from the fermentation medium, cell debris originating from the production host cells, metabolites produced by the production host cells during fermentation. In one embodiment, residual components may be comprised in liquid enzyme concentrates in amounts less than 30% by weight, less than 20% by weight less, than 10% by weight, or less than 5% by weight, all relative to the total weight of the aqueous enzyme concentrate.

At least one enzyme comprised in component (b) is selected from hydrolases (EC 3), hereinafter also referred to as enzyme (component (b)). Preferred enzymes (component (b)) are selected from the group of enzymes acting on ester bond (E.C. 3.1), glycosylases (E.C. 3.2), and peptidases (E.C. 3.4). Enzymes acting on ester bond (E.C. 3.1), are hereinafter also referred to as lipases (component (b)), respectively. Glycosylases (E.C. 3.2) are hereinafter also referred to as either amylases (component (b)) and cellulases (component (b)). Peptidases are hereinafter also referred to as proteases (component (b)).

Hydrolases (component (b)) in the context of the present invention are identified by polypeptide sequences (also called amino acid sequences herein). The polypeptide sequence specifies the three-dimensional structure including the "active site" of an enzyme which in turn determines the catalytic activity of the same. Polypeptide sequences may be identified by a SEQ ID NO. According to the World Intellectual Property Office (WIPO) Standard ST.25 (1998) the amino acids herein are represented using three-letter code with the first letter as a capital or the corresponding one letter.

The enzyme (component (b)) according to the invention relates to parent enzymes and/or variant enzymes, both having enzymatic activity. Enzymes having enzymatic activity are enzymatically active or exert enzymatic conversion, meaning that enzymes act on substrates and convert these into products. The term "enzyme" herein excludes inactive variants of an enzyme.

A "parent" sequence (of a parent protein or enzyme, also called "parent enzyme") is the starting sequence for introduction of changes (e.g. by introducing one or more amino acid substitutions, insertions, deletions, or a combination thereof) to the sequence, resulting in "variants" of the parent sequences. The term parent enzyme (or parent sequence) includes wild-type enzymes (sequences) and synthetically generated sequences (enzymes) which are used as starting sequences for introduction of (further) changes.

The term "enzyme variant" or "sequence variant" or "variant enzyme" refers to an enzyme that differs from its parent enzyme in its amino acid sequence to a certain extent. If not indicated otherwise, variant enzyme "having enzymatic activity" means that this variant enzyme has the same type of enzymatic activity as the respective parent enzyme.

In describing the variants of the present invention, the nomenclature described as follows is used:

Amino acid substitutions are described by providing the original amino acid of the parent enzyme followed by the number of the position within the amino acid sequence, followed by the substituted amino acid.

Amino acid deletions are described by providing the original amino acid of the parent enzyme followed by the number of the position within the amino acid sequence, followed by *.

Amino acid insertions are described by providing the original amino acid of the parent enzyme followed by the number of the position within the amino acid sequence, followed by the original amino acid and the additional amino acid. For example, an insertion at position 180 of lysine next to glycine is designated as "Gly180GlyLys" or "G180GK".

In cases where a substitution and an insertion occur at the same position, this may be indicated as S99SD+S99A or in short S99AD. In cases where an amino acid residue identical to the existing amino acid residue is inserted, it is clear that degeneracy in the nomenclature arises. If for example a glycine is inserted after the glycine in the above example this would be indicated by G180GG.

Where different alterations can be introduced at a position, the different alterations are separated by a comma, e.g. "Arg170Tyr, Glu" represents a substitution of arginine at position 170 with tyrosine or glutamic acid. Alternatively different alterations or optional substitutions may be indicated in brackets e.g. Arg170[Tyr, Gly] or Arg170{Tyr, Gly}; or in short R170 [Y,G] or R170 {Y, G}; or in long R170Y, R170G.

Enzyme variants may be defined by their sequence identity when compared to a parent enzyme. Sequence identity usually is provided as "% sequence identity" or "% identity". For calculation of sequence identities, in a first step a sequence alignment has to be produced. According to this invention, a pairwise global alignment has to be produced, meaning that two sequences have to be aligned over their complete length, which is usually produced by using a mathematical approach, called alignment algorithm.

According to the invention, the alignment is generated by using the algorithm of Needleman and Wunsch (J. Mol. Biol. (1979) 48, p. 443-453). Preferably, the program "NEEDLE" (The European Molecular Biology Open Software Suite (EMBOSS)) is used for the purposes of the current invention, with using the programs default parameter (gap open=10.0, gap extend=0.5 and matrix=EBLOSUM62).

According to this invention, the following calculation of %-identity applies: %-identity=(identical residues/length of the alignment region which is showing the respective sequence of this invention over its complete length)*100.

According to this invention, enzyme variants may be described as an amino acid sequence which is at least n % identical to the amino acid sequence of the respective parent enzyme with "n" being an integer between 10 and 100. In one embodiment, variant enzymes are at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical when compared to the full length amino acid sequence of the parent enzyme, wherein the enzyme variant has enzymatic activity.

Enzyme variants may be defined by their sequence similarity when compared to a parent enzyme. Sequence similarity usually is provided as "% sequence similarity" or "%-similarity". % sequence similarity takes into account that defined sets of amino acids share similar properties, e.g by their size, by their hydrophobicity, by their charge, or by other characteristics. Herein, the exchange of one amino acid with a similar amino acid may be called "conservative mutation".

For determination of %-similarity according to this invention the following applies: amino acid A is similar to amino acids S; amino acid D is similar to amino acids E and N; amino acid E is similar to amino acids D and K and Q; amino acid F is similar to amino acids W and Y; amino acid H is similar to amino acids N and Y; amino acid I is similar to amino acids L and M and V; amino acid K is similar to amino acids E and Q and R; amino acid L is similar to amino acids I and M and V; amino acid M is similar to amino acids I and L and V; amino acid N is similar to amino acids D and H and S; amino acid Q is similar to amino acids E and K and R; amino acid R is similar to amino acids K and Q; amino acid S is similar to amino acids A and N and T; amino acid T is similar to amino acids S; amino acid V is similar to amino acids I and L and M; amino acid W is similar to amino acids F and Y; amino acid Y is similar to amino acids F and H and W.

Conservative amino acid substitutions may occur over the full length of the sequence of a polypeptide sequence of a functional protein such as an enzyme. In one embodiment, such mutations are not pertaining the functional domains of an enzyme. In one embodiment, conservative mutations are not pertaining the catalytic centers of an enzyme.

To take conservative mutations into account, a value for sequence similarity of two amino acid sequences may be calculated from the same alignment, which is used to calculate %-identity.

According to this invention, the following calculation of %-similarity applies: %-similarity=[(identical residues+similar residues)/length of the alignment region which is showing the respective sequence(s) of this invention over its complete length]*100.

According to this invention, enzyme variants may be described as an amino acid sequence which is at least m % similar to the respective parent sequences with "m" being an integer between 10 and 100. In one embodiment, variant enzymes are at least 70%, at least 75%, at least 80%, at least 85%, at least 90%, at least 91%, at least 92%, at least 93%, at least 94%, at least 95%, at least 96%, at least 97%, at least 98%, or at least 99% similar when compared to the full length polypeptide sequence of the parent enzyme, wherein the variant enzyme has enzymatic activity.

"Enzymatic activity" means the catalytic effect exerted by an enzyme, which usually is ex-pressed as units per milligram of enzyme (specific activity) which relates to molecules of substrate transformed per minute per molecule of enzyme (molecular activity).

Variant enzymes may have enzymatic activity according to the present invention when said enzyme variants exhibit at least 20%, at least 25%, at least 30%, at least 35%, at least 40%, at least 45%, at 10 least 50%, at least 55%, at least 60%, at least 65%, at least 70%, at least 75%, at least 80%, at least 85%, at least 90%, at least 95%, or 100% of the enzymatic activity of the respective parent enzyme.

At least one enzyme comprised in component (b) is selected from the group of hydrolases (EC 3).

Lipase

In one embodiment, inventive enzyme preparations comprise at least one lipase (EC 3.1.1; component (b)). "Lipases", "lipolytic enzyme", "lipid esterase", all refer to an enzyme of EC class 3.1.1 ("carboxylic ester hydrolase"). Lipase means active protein having lipase activity (or lipolytic activity; triacylglycerol lipase, EC 3.1.1.3), cutinase activity (EC 3.1.1.74; enzymes having cutinase activity may be called cutinase herein), sterol esterase activity (EC 3.1.1.13) and/or wax-ester hydrolase activity (EC 3.1.1.50).

The methods for determining lipolytic activity are well-known in the literature (see e.g. Gupta et al. (2003), Biotechnol. Appl. Biochem. 37, p. 63-71). E.g. the lipase activity may be measured by ester bond hydrolysis in the substrate para-nitrophenyl palmitate (pNP-Palmitate, C:16) and releases pNP which is yellow and can be detected at 405 nm.

"Lipolytic activity" means the catalytic effect exerted by a lipase, which may be provided in lipolytic units (LU). For example, 1 LU may correspond to the amount of lipase which produces 1 µmol of titratable fatty acid per minute in a pH stat. under the following conditions: temperature 30° C.; pH=9.0; substrate may be an emulsion of 3.3 wt. % of olive oil and 3.3% gum arabic, in the presence of 13 mmol/l $Ca^{2+}$ and 20 mmol/l NaCl in 5 mmol/l Tris-buffer.

Lipases (component (b)) include those of bacterial or fungal origin. In one aspect of the invention, a suitable lipase (component (b)) is selected from the following: lipases from *Humicola* (synonym *Thermomyces*), e.g. from *H. lanuginosa* (*T lanuginosus*) as described in EP 258068, EP 305216, WO 92/05249 and WO 2009/109500 or from *H. insolens* as described in WO 96/13580; lipases derived from *Rhizomucor miehei* as described in WO 92/05249; lipase from strains of *Pseudomonas* (some of these now renamed to *Burkholderia*), e.g. from *P. alcaligenes* or *P. pseudoalcaligenes* (EP 218272, WO 94/25578, WO 95/30744, WO 95/35381, WO 96/00292), *P. cepacia* (EP 331376), *P. stutzeri* (GB 1372034), *P. fluorescens, Pseudomonas* sp. strain SD705 (WO 95/06720 and WO 96/27002), *P. wisconsinensis* (WO 96/12012), *Pseudomonas mendocina* (WO 95/14783), *P. glumae* (WO 95/35381, WO 96/00292); lipase from *Streptomyces griseus* (WO 2011/150157) and *S. pristinaespiralis* (WO 2012/137147), GDSL-type *Streptomyces* lipases (WO 2010/065455); lipase from *Thermobifida fusca* as disclosed in WO 2011/084412; lipase from *Geobacillus stearothermophilus* as disclosed in WO 2011/084417; *Bacillus* lipases, e.g. as disclosed in WO 00/60063, lipases from *B. subtilis* as disclosed in Dartois et al. (1992), Biochemica et Biophysica Acta, 1131, 253-360 or WO 2011/084599, *B. stearothermophilus* (JP 564-074992) or *B. pumilus* (WO 91/16422); lipase from *Candida antarctica* as disclosed in WO 94/01541; cutinase from *Pseudomonas mendocina* (U.S. Pat. No. 5,389,536, WO 88/09367); cutinase from *Magnaporthe grisea* (WO 2010/107560); cutinase from *Fusarium solanipisias* disclosed in WO 90/09446, WO 00/34450 and WO 01/92502; and cutinase from *Humicola lanuginosa* as disclosed in WO 00/34450 and WO 01/92502.

Suitable lipases (component (b)) also include those referred to as acyltransferases or perhydrolases, e.g. acyltransferases with homology to *Candida antarctica* lipase A (WO 2010/111143), acyltransferase from *Mycobacterium smegmatis* (WO 2005/056782), perhydrolases from the CE7 family (WO 2009/67279), and variants of the *M. smegmatis* perhydrolase in particular the S54V variant (WO 2010/100028).

Suitable lipases (component (b)) include also those which are variants of the above described lipases which have lipolytic activity. Such suitable lipase variants (component (b)) are e.g. those which are developed by methods as disclosed in WO 95/22615, WO 97/04079, WO 97/07202, WO 00/60063, WO 2007/087508, EP 407225 and EP 260105.

Suitable lipases (component (b)) include lipase variants having lipolytic activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical when compared to the full length polypeptide sequence of the parent enzyme as disclosed above.

Suitable lipases (component (b)) include lipase variants having lipolytic activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% similar when compared to the full length polypeptide sequence of the parent enzyme.

In one embodiment, lipase (component (b)) is selected from fungal triacylglycerol lipase (EC class 3.1.1.3). Fungal triacylglycerol lipase (component (b)) may be selected from lipase of *Thermomyces lanuginosa*. In one embodiment, *Thermomyces lanuginosa* lipase (component (b)) is selected from triacylglycerol lipase according to amino acids 1-269 of SEQ ID NO:2 of U.S. Pat. No. 5,869,438 and variants thereof having lipolytic activity. Triacylglycerol lipase according to amino acids 1-269 of SEQ ID NO:2 of U.S. Pat. No. 5,869,438 may be called Lipolase herein.

*Thermomyces lanuginosa* lipase (component (b)) may be selected from variants having lipolytic activity which are at least 90%, at least 91%, at least 92%, at least 93%, at least 94%, at least 95%, at least 96%, at least 97%, at least 98% or at least 99% identical when compared to the full length polypeptide sequence of amino acids 1-269 of SEQ ID NO:2 of U.S. Pat. No. 5,869,438.

*Thermomyces lanuginosa* lipase (component (b)) may be selected from variants having lipolytic activity comprising conservative mutations only, which do however not pertain the functional domain of amino acids 1-269 of SEQ ID NO:2 of U.S. Pat. No. 5,869,438. Lipase variants of this embodiment having lipolytic activity may be at least 95%, at least 96%, at least 97%, at least 98% or at least 99% similar when compared to the full length polypeptide sequence of amino acids 1-269 of SEQ ID NO:2 of U.S. Pat. No. 5,869,438.

*Thermomyces lanuginosa* lipase (component (b)) may be at least 80% identical to SEQ ID NO:2 of U.S. Pat. No. 5,869,438 characterized by having amino acid T231R and N233R. Said *Thermomyces lanuginosa* lipase may further comprise one or more of the following amino acid exchanges: Q4V, V60S, A150G, L227G, P256K.

In one embodiment, at least one lipase is selected from commercially available lipases which include but are not limited to products sold under the trade names Lipolase™, Lipex™, Lipolex™ and Lipoclean™ (Novozymes A/S), Lumafast (originally from Genencor) and Lipomax (Gist-Brocades/now DSM).

According to the present invention, component (b) may comprise a combination of at least two lipases, preferably selected from the group of triacylglycerol lipase (EC 3.1.1.3).

In one embodiment, component (b) comprises at least one lipase selected from triacylglycerol lipase according to amino acids 1-269 of SEQ ID NO:2 of U.S. Pat. No. 5,869,438 and variants thereof having lipolytic activity as disclosed above.

In one embodiment, component (b) comprises a combination of at least one lipase, preferably selected from the group of triacylglycerol lipase (EC 3.1.1.3), and at least one protease, preferably selected from serine endopeptidases (EC 3.4.21), more preferably selected from the group of subtilisin type proteases (EC 3.4.21.62).

Protease

In one embodiment, inventive enzyme preparations comprise at least one protease (component (b)). Proteases are members of class EC 3.4. Proteases (component (b)) include aminopeptidases (EC 3.4.11), dipeptidases (EC 3.4.13), dipeptidyl-peptidases and tripeptidyl-peptidases (EC 3.4.14), peptidyl-dipeptidases (EC 3.4.15), serine-type carboxypeptidases (EC 3.4.16), me-tallocarboxypeptidases (EC 3.4.17), cysteine-type carboxypeptidases (EC 3.4.18), omega peptidases (EC 3.4.19), serine endopeptidases (EC 3.4.21), cysteine endopeptidases (EC 3.4.22), aspartic endopeptidases (EC 3.4.23), metallo-endopeptidases (EC 3.4.24), threonine endopeptidases (EC 3.4.25), or endopeptidases of unknown catalytic mechanism (EC 3.4.99).

In one embodiment, at least one protease (component (b)) is selected from serine proteases (EC 3.4.21). Serine proteases or serine peptidases are characterized by having a serine in the catalytically active site, which forms a covalent adduct with the substrate during the catalytic reaction. A serine protease (component (b)) in the context of the present invention is selected from the group consisting of chymotrypsin (e.g., EC 3.4.21.1), elastase (e.g., EC 3.4.21.36), elastase (e.g., EC 3.4.21.37 or EC 3.4.21.71), granzyme (e.g., EC 3.4.21.78 or EC 3.4.21.79), kallikrein (e.g., EC 3.4.21.34, EC 3.4.21.35, EC 3.4.21.118, or EC 3.4.21.119) plasmin (e.g., EC 3.4.21.7), trypsin (e.g., EC 3.4.21.4), thrombin (e.g., EC 3.4.21.5), and subtilisin. Subtilisin is also known as subtilopeptidase, e.g., EC 3.4.21.62, the latter hereinafter also being referred to as "subtilisin".

A sub-group of the serine proteases tentatively designated as subtilases has been proposed by Siezen et al. (1991), Protein Eng. 4:719-737 and Siezen et al. (1997), Protein Science 6:501-523. Subtilases includes the subtilisin family, thermitase family, the proteinase K family, the lantibiotic peptidase family, the kexin family and the pyrolysin family.

A subgroup of the subtilases are the subtilisins which are serine proteases from the family S8 as defined by the MEROPS database (http://merops.sanger.ac.uk). Peptidase family S8 contains the serine endopeptidase subtilisin and its homologues. In subfamily S8A, the active site residues frequently occur in the motifs Asp-Thr/Ser-Gly (which is similar to the sequence motif in families of aspartic endopeptidases in clan AA), His-Gly-Thr-His and Gly-Thr-Ser-Met-Ala-Xaa-Pro.

The subtilisin related class of serine proteases (component (b)) shares a common amino acid sequence defining a catalytic triad which distinguishes them from the chymotrypsin related class of serine proteases. Subtilisins and chymotrypsin related serine proteases both have a catalytic triad comprising aspartate, histidine and serine.

Examples include the subtilisins as described in WO 89/06276 and EP 0283075, WO 89/06279, WO 89/09830, WO 89/09819, WO 91/06637 and WO 91/02792.

Proteases are active proteins exerting "protease activity" or "proteolytic activity". Proteolytic activity is related to the rate of degradation of protein by a protease or proteolytic enzyme in a defined course of time.

The methods for analyzing proteolytic activity are well-known in the literature (see e.g. Gupta et al. (2002), Appl. Microbiol. Biotechnol. 60: 381-395). Proteolytic activity may be determined by using Succinyl-Ala-Ala-Pro-Phe-p-nitroanilide (Suc-AAPF-pNA, short AAPF; see e.g. DelMar et al. (1979), Analytical Biochem 99, 316-320) as substrate. pNA is cleaved from the substrate molecule by proteolytic cleavage, resulting in release of yellow color of free pNA which can be quantified by measuring $OD_{405}$.

Proteolytic activity may be provided in units per gram enzyme. For example, 1 U protease may correspond to the amount of protease which sets free 1 μmol folin-positive amino acids and peptides (as tyrosine) per minute at pH 8.0 and 37° C. (casein as substrate).

Proteases (component (b)) of the subtilisin type (EC 3.4.21.62) may be bacterial proteases originating from a microorganism selected from *Bacillus, Clostridium, Enterococcus, Geobacillus, Lactobacillus, Lactococcus, Oceanobacillus, Staphylococcus, Streptococcus*, or *Streptomyces* protease, or a Gram-negative bacterial polypeptide such as a *Campylobacter, E. coli, Flavobacterium, Fusobacterium, Helicobacter, Ilyobacter, Neisseria, Pseudomonas, Salmonella*, and *Ureaplasma*.

In one aspect of the invention, at least one protease (component (b)) is selected from *Bacillus alcalophilus, Bacillus amyloliquefaciens, Bacillus brevis, Bacillus circulans, Bacillus clausii, Bacillus coagulans, Bacillus firmus, Bacillus gibsonii Bacillus lautus, Bacillus lentus, Bacillus licheniformis, Bacillus megaterium, Bacillus pumilus, Bacillus sphaericus, Bacillus stearothermophilus, Bacillus subtilis*, or *Bacillus thuringiensis* protease.

In one embodiment of the present invention, at least one protease (component (b)) is selected from the following: subtilisin from *Bacillus amyloliquefaciens* BPN' (described by Vasantha et al. (1984) J. Bacteriol. Volume 159, p. 811-819 and JA Wells et al. (1983) in Nucleic Acids Research, Volume 11, p. 7911-7925); subtilisin from *Bacillus licheniformis* (subtilisin Carlsberg; disclosed in E L Smith et al. (1968) in J. Biol Chem, Volume 243, pp. 2184-2191, and Jacobs et al. (1985) in Nucl. Acids Res, Vol 13, p. 8913-8926); subtilisin PB92 (original sequence of the alkaline protease PB92 is described in EP 283075 A2); subtilisin 147 and/or 309 (Esperase®, Savinase®, respectively) as disclosed in WO 89/06279; subtilisin from *Bacillus lentus* as disclosed in WO 91/02792, such as from *Bacillus lentus* DSM 5483 or the variants of *Bacillus lentus* DSM 5483 as described in WO 95/23221; subtilisin from *Bacillus alcalophilus* (DSM 11233) disclosed in DE 10064983; subtilisin from *Bacillus gibsonii*(DSM 14391) as disclosed in WO 2003/054184; subtilisin from *Bacillus* sp. (DSM 14390) disclosed in WO 2003/056017; subtilisin from *Bacillus* sp. (DSM 14392) disclosed in WO 2003/055974; subtilisin from *Bacillus gibsonii* (DSM 14393) disclosed in WO 2003/054184; subtilisin having SEQ ID NO: 4 as described in WO 2005/063974; subtilisin having SEQ ID NO: 4 as described in WO 2005/103244; subtilisin having SEQ ID NO: 7 as described in WO 2005/103244; and subtilisin having SEQ ID NO: 2 as described in application DE 102005028295.4.

In one embodiment, component (b) comprises at least subtilisin 309 (which might be called Savinase herein) as disclosed as sequence a) in Table I of WO 89/06279 or a variant which is at least 80% identical thereto and has proteolytic activity.

Examples of useful proteases (component (b)) in accordance with the present invention comprise the variants described in: WO 92/19729, WO 95/23221, WO 96/34946, WO 98/20115, WO 98/20116, WO 99/11768, WO 01/44452, WO 02/088340, WO 03/006602, WO 2004/03186, WO 2004/041979, WO 2007/006305, WO 2011/036263, WO 2011/036264, and WO 2011/072099. Suitable examples comprise especially variants of subtilisin protease derived from SEQ ID NO:22 as described in EP 1921147 (which is the sequence of mature alkaline protease from *Bacillus lentus* DSM 5483) with amino acid substitutions in one or more of the following positions: 3, 4, 9, 15, 24, 27, 33, 36, 57, 68, 76, 77, 87, 95, 96, 97, 98, 99, 100, 101, 102, 103, 104, 106, 118, 120, 123, 128, 129, 130, 131, 154, 160, 167, 170, 194, 195, 199, 205, 206, 217, 218, 222, 224, 232, 235, 236, 245, 248, 252 and 274 (according to the BPN' numbering), which have proteolytic activity. In one embodiment, such a protease is not mutated at positions Asp32, His64 and Ser221 (according to BPN' numbering).

Suitable proteases (component (b)) include protease variants having proteolytic activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical when compared to the full length polypeptide sequence of the parent enzyme as disclosed above.

Suitable proteases (component (b)) include protease variants having proteolytic activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% similar when compared to the full length polypeptide sequence of the parent enzyme.

In one embodiment, at least one protease (component (b)) has SEQ ID NO:22 as described in EP 1921147, or a protease which is at least 80% identical thereto and has proteolytic activity. In one embodiment, said protease is characterized by having amino acid glutamic acid (E), or aspartic acid (D), or asparagine (N), or glutamine (Q), or alanine (A), or glycine (G), or serine (S) at position 101 (according to BPN' numbering) and has proteolytic activity. In one embodiment, said protease comprises one or more further substitutions: (a) threonine at position 3 (3T), (b) isoleucine at position 4 (4I), (c) alanine, threonine or arginine at position 63 (63A, 63T, or 63R), (d) aspartic acid or glutamic acid at position 156 (156D or 156E), (e) proline at position 194 (194P), (f) methionine at position 199 (199M), (g) isoleucine at position 205 (205I), (h) aspartic acid, glutamic acid or glycine at position 217 (217D, 217E or 217G), (i) combinations of two or more amino acids according to (a) to (h). At least one protease (component (b)) may be at least 80% identical to SEQ ID NO:22 as described in EP 1921147 and is characterized by comprising one amino acid (according to (a)-(h)) or combinations according to (i) together with the amino acid 101E, 101D, 101N, 101Q, 101A, 101G, or 101S (according to BPN' numbering) and having proteolytic activity. In one embodiment, said protease is characterized by comprising the mutation (according to BPN' numbering) R101E, or S3T+V4I+V205I, or R101E and S3T, V4I, and V205I, or S3T+V4I+V199M+V205I+L217D, and having proteolytic activity.

In one embodiment, protease according to SEQ ID NO:22 as described in EP 1921147 is characterized by comprising the mutation (according to BPN' numbering) S3T+V4I+S9R+A15T+V68A+D99S+R101S+A103S+I104V+N218D, and having proteolytic activity.

In one embodiment, at least one protease is selected from commercially available protease enzymes which include but are not limited to products sold under the trade names Alcalase®, Blaze®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect® Prime, Purafect MA®, Purafect Ox®, Purafect OxP®, Puramax®, Properase®, FN2®, FN3®, FN4®, Excellase®, Eraser@, Ultimase®, Opticlean®, Effectenz®, Preferenz® and Optimase® (Danisco/DuPont), Axapem™ (Gist-Brocases N.V.), *Bacillus lentus* Alkaline Protease (BLAP; sequence shown in FIG. 29 of U.S. Pat. No. 5,352,604) and variants thereof and KAP (*Bacillus alkalophilus* subtilisin) from Kao Corp.

According to the present invention, component (b) may comprise a combination of at least two proteases, preferably selected from the group of serine endopeptidases (EC 3.4.21), more preferably selected from the group of subtilisin type proteases (EC 3.4.21.62)—all as disclosed above.

In one embodiment, component (b) comprises a combination of at least one lipase and at least one protease. In one embodiment, component (b) comprises at least one lipase selected from triacylglycerol lipase (EC 3.1.1.3), and at least one protease selected from the group of serine endopeptidases (EC 3.4.21), more preferably selected from the group of subtilisin type proteases (EC 3.4.21.62).

In one embodiment, component (b) comprises at least one lipase selected from triacylglycerol lipase (EC 3.1.1.3), and at least one protease selected from proteases according to SEQ ID NO:22 as described in EP 1921147 or variants thereof having proteolytic activity—all as disclosed above.

In one embodiment, component (b) comprises at least one lipase selected from triacylglycerol lipase according to amino acids 1-269 of SEQ ID NO:2 of U.S. Pat. No. 5,869,438 and variants thereof having lipolytic activity, and at least one protease selected from proteases according to SEQ ID NO:22 as described in EP 1921147 or variants thereof having proteolytic activity—all as disclosed above.

In one embodiment, component (b) comprises at least one lipase selected from triacylglycerol lipase according to amino acids 1-269 of SEQ ID NO:2 of U.S. Pat. No. 5,869,438 and variants thereof having lipolytic activity, and at least one protease selected from subtilisin 309 as disclosed in Table I a) of WO 89/06279 or variants thereof having proteolytic activity—all as disclosed above.

Amylase

In one embodiment, inventive enzyme preparations comprise at least one amylase (component (b)). "Amylases" (component (b)) according to the invention (alpha and/or beta) include those of bacterial or fungal origin (EC 3.2.1.1 and 3.2.1.2, respectively). Chemically modified or protein engineered mutants are included.

Amylases (component (b)) according to the invention have "amylolytic activity" or "amylase activity" involving (endo)hydrolysis of glucosidic linkages in polysaccharides. α-amylase activity may be determined by assays for measurement of α-amylase activity which are known to those skilled in the art. Examples for assays measuring α-amylase activity are:

α-amylase activity can be determined by a method employing Phadebas tablets as substrate (Phadebas Amylase Test, supplied by Magle Life Science). Starch is hydrolyzed by the α-amylase giving soluble blue fragments. The absorbance of the resulting blue solution, measured spectrophotometrically at 620 nm, is a function of the α-amylase activity. The measured absorbance is directly proportional to the specific activity (activity/mg of pure α-amylase protein) of the α-amylase in question under the given set of conditions.

α-amylase activity can also be determined by a method employing the Ethyliden-4-nitrophenyl-α-D-maltoheptaosid (EPS). D-maltoheptaoside is a blocked oligosaccharide which can be cleaved by an endo-amylase. Following the cleavage, the α-glucosidase included in the kit to digest the substrate to liberate a free PNP molecule which has a yellow color and thus can be measured by visible spectophotometry at 405 nm. Kits containing EPS substrate and α-glucosidase is manufactured by Roche Costum Biotech (cat. No. 10880078103). The slope of the time dependent absorption-curve is directly proportional to the specific activity (activity per mg enzyme) of the α-amylase in question under the given set of conditions.

Amylolytic activity may be provided in units per gram enzyme. For example, 1 unit α-amylase may liberate 1.0 mg of maltose from starch in 3 min at pH 6.9 at 20° C.

At least one amylase (component (b)) may be selected from the following: amylases from *Bacillus licheniformis* having SEQ ID NO:2 as described in WO 95/10603; amylases from *B. stearothermophilus* having SEQ ID NO:6 as disclosed in WO 02/10355; amylases from *Bacillus* sp.707 having SEQ ID NO:6 as disclosed in WO 99/19467; amylases from *Bacillus halmapalus* having SEQ ID NO:2 or SEQ ID NO:7 as described in WO 96/23872, also described as SP-722; amylases from *Bacillus* sp. DSM 12649 having SEQ ID NO:4 as disclosed in WO 00/22103; amylases from *Bacillus* strain TS-23 having SEQ ID NO:2 as disclosed in WO 2009/061380; amylases from *Cytophaga* sp. having SEQ ID NO:1 as disclosed in WO 2013/184577; amylases from *Bacillus megaterium* DSM 90 having SEQ ID NO:1 as disclosed in WO 2010/104675; amylases from *Bacillus* sp. comprising amino acids 1 to 485 of SEQ ID NO:2 as described in WO 00/60060.

Suitable amylases (component (b)) include amylase variants having amylase activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% identical when compared to the full length polypeptide sequence of the parent enzyme as disclosed above.

Suitable amylases (component (b)) include amylase variants having amylase activity which are at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% similar when compared to the full length polypeptide sequence of the parent enzyme.

At least one amylase (component (b)) may have SEQ ID NO: 12 as described in WO 2006/002643 or is at least 80% identical thereto and has amylolytic activity. At least one amylase may be at least 80% identical to SEQ ID NO:12 and comprises the substitutions at positions Y295F and M202LITV.

At least one amylase (component (b)) may have SEQ ID NO:6 as described in WO 2011/098531 or is at least 80% identical thereto and has amylolytic activity. At least one amylase may be at least 80% identical to SEQ ID NO:6 and comprises a substitution at one or more positions selected from the group consisting of 193 [G,A,S,T or M], 195 [F,W,Y,L,I or V], 197 [F,W,Y,L,I or V], 198 [Q or N], 200 [F,W,Y,L,I or V], 203 [F,W,Y,L,I or V], 206 [F,W,Y,N,L,I,V,H,Q,D or E], 210 [F,W,Y,L,I or V], 212 [F,W,Y,L,I or V], 213 [G,A,S,T or M] and 243 [F,W,Y,L,I or V].

At least one amylase (component (b)) may have SEQ ID NO:1 as described in WO 2013/001078 or is at least 85% identical thereto and has amylolytic activity. At least one amylase may be at least 85% identical to SEQ ID NO:1 and comprises an alteration at two or more (several) positions corresponding to positions G304, W140, W189, D134, E260, F262, W284, W347, W439, W469, G476, and G477.

At least one amylase (component (b)) may have SEQ ID NO:2 as described in WO 2013/001087 or is at least 85% identical thereto and has amylolytic activity. At least one amylase may be at least 85% identical to SEQ ID NO:2 and comprises a deletion of positions 181+182, or 182+183, or 183+184, and has amylolytic activity. In one embodiment, said amylase may comprise one or two or more further modifications in any of positions corresponding to W140, W159, W167, Q169, W189, E194, N260, F262, W284, F289, G304, G305, R320, W347, W439, W469, G476 and G477.

In one embodiment, at least one amylase is selected from commercially available amylases which include but are not limited to products sold under the trade names Duramyl™, Termamyl™, Fungamyl™, Stainzyme™, Stainzyme Plus™, Natalase™, Liquozyme X and BAN™ (from Novozymes A/S), and Rapidase™, Purastar™, Powerase™, Effectenz™ (M100 from DuPont), Preferenz™ (S1000, S110 and F1000; from DuPont), PrimaGreen™ (ALL; DuPont), Optisize™ (DuPont).

According to the present invention, a combination of at least two amylases (component (b)) may be used.

In one embodiment, component (b) comprises a combination of at least one lipase and at least one amylase.

In one embodiment, component (b) comprises a combination of at least one protease and/or at least one amylase.

In one embodiment, component (b) comprises a combination of at least one lipase and at least one protease and at least one amylase.

Cellulase

The enzyme preparation of the invention may comprise at least one cellulase (component (b)). Three major types of cellulases are known, namely cellobiohydrolase (1,4-P-D-glucan cellobiohydrolase, EC 3.2.1.91), endo-ss-1,4-glucanase (endo-1,4-P-D-glucan 4-glucanohydrolase, EC 3.2.1.4) and ss-glucosidase (EC 3.2.1.21).

"Cellulases", "cellulase enzymes" or "cellulolytic enzymes" (component (b)) are enzymes involved in hydrolysis of cellulose. Assays for measurement of "cellulase activity" or "cellulolytic activity" are known to those skilled in the art. For example, cellulolytic activity may be determined by virtue of the fact that cellulase hydrolyses carboxymethyl cellulose to reducing carbo-hydrates, the reducing ability of which is determined colorimetrically by means of the ferricyanide reaction, according to Hoffman, W. S., J. Biol. Chem. 120, 51 (1937).

Cellulolytic activity may be provided in units per gram enzyme. For example, 1 unit may liberate 1.0 μmole of glucose from cellulose in one hour at pH 5.0 at 37° C. (2 hour incubation time).

Cellulases according to the invention include those of bacterial or fungal origin.

In one embodiment, at least one cellulase (component (b)) is selected from commercially available cellulases which include but are not limited to Celluzyme™, Endolase™, Carezyme™, Cellusoft™, Renozyme™, Celluclean™ (from Novozymes A/S), Ecostone™, Biotouch™, Econase™, Ecopulp™ (from AB Enzymes Finland), Clazinase™, and Puradax HA™, Genencor detergent cellulase L, IndiAge™ Neutra (from Genencor International Inc./DuPont), Revitalenz™ (2000 from DuPont), Primafast™ (DuPont) and KAC-500™ (from Kao Corporation).

Component (c)

In one embodiment, the liquid enzyme preparation of the invention contains component (c) which comprises at least one compound selected from enzyme stabilizers different from component (a), preservatives, and surfactants.

Enzyme Stabilizers Different from Component (a):

The liquid enzyme preparation of the invention may comprise at least one enzyme stabilizer different from component (a). Said enzyme stabilizer (component (c)) may be selected from boron-containing compounds, polyols, peptide aldehydes, other stabilizers, and mixtures thereof.

Boron-Containing Compounds.

Boron-containing compounds (component (c)) may be selected from boric acid or its derivatives and from boronic acid or its derivatives such as aryl boronic acids or its derivatives, from salts thereof, and from mixtures thereof. Boric acid herein may be called orthoboric acid.

In one embodiment, boron-containing compound (component (c)) is selected from the group consisting of aryl boronic acids and its derivatives. In one embodiment, boron-containing compound is selected from the group consisting of benzene boronic acid (BBA) which is also called phenyl boronic acid (PBA), derivatives thereof, and mixtures thereof. In one embodiment, phenyl boronic acid derivatives are selected from the group consisting of the derivatives of formula (IIIa) and (IIIb) formula:

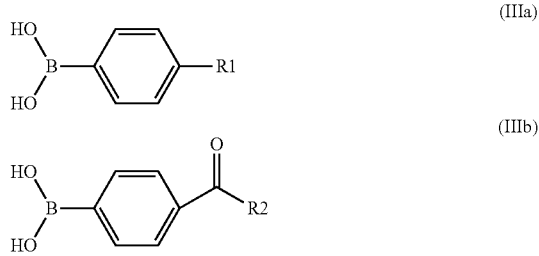

wherein
R1 is selected from the group consisting of hydrogen, hydroxy, non-substituted or substituted $C_1$-$C_6$ alkyl, and non-substituted or substituted $C_1$-$C_6$ alkenyl; in a preferred embodiment, R is selected from the group consisting of hydroxy, and non-substituted $C_1$ alkyl;
R2 is selected from the group consisting of hydrogen, hydroxy, non-substituted or substituted $C_1$-$C_6$ alkyl, and non-substituted or substituted $C_1$-$C_6$ alkenyl; in a preferred embodiment, R is selected from the group consisting of H, hydroxy, and substituted $C_1$ alkyl.

In one embodiment phenyl-boronic acid derivatives (component (c)) are selected from the group consisting of 4-formyl phenyl boronic acid (4-FPBA), 4-carboxy phenyl boronic acid (4-CPBA), 4-(hydroxymethyl) phenyl boronic acid (4-HMPBA), and p-tolylboronic acid (p-TBA).

Other suitable derivatives (component (c)) include: 2-thienyl boronic acid, 3-thienyl boronic acid, (2-acetamidophenyl) boronic acid, 2-benzofuranyl boronic acid, 1-naphthyl boronic acid, 2-naphthyl boronic acid, 2-FPBA, 3-FBPA, 1-thianthrenyl boronic acid, 4-dibenzofuran boronic acid, 5-methyl-2-thienyl boronic acid, 1-benzothiophene-2 boronic acid, 2-furanyl boronic acid, 3-furanyl boronic acid, 4,4 biphenyl-diboronic acid, 6-hydroxy-2-naphthaleneboronic acid, 4-(methylthio) phenyl boronic acid, 4-(trimethylsilyl) phenyl boronic acid, 3-bromothiophene boronic acid, 4-methylthiophene boronic acid, 2-naphthyl boronic acid, 5-bromothiophene boronic acid, 5-chlorothiophene boronic acid, dimethylthiophene boronic acid, 2-bromophenyl boronic acid, 3-chlorophenyl boronic acid, 3-methoxy-2-thiophene boronic acid, p-methyl-phenylethyl boronic acid, 2-thianthrenyl boronic acid, di-benzothiophene boronic acid, 9-anthracene boronic acid, 3,5 dichlorophenyl boronic, acid, diphenyl boronic acid anhydride, o-chlorophenyl boronic acid, p-chlorophenyl boronic acid, m-bromophenyl boronic acid, p-bromophenyl boronic acid, p-fluorophenyl boronic acid, octyl boronic acid, 1,3,5 trimethylphenyl boronic acid, 3-chloro-4-fluorophenyl boronic acid, 3-aminophenyl boronic acid, 3,5-bis-(trifluoromethyl) phenyl boronic acid, 2,4 dichlorophenyl boronic acid, 4-methoxyphenyl boronic acid, and mixtures thereof.

Polyols.

Polyols (component (c)) may be selected from polyols containing from 2 to 6 hydroxyl groups. Suitable examples include glycol, propylene glycol, 1,2-propane diol, 1,2-butane diol, ethylene glycol, hexylene glycol, glycerol, sorbitol, mannitol, erythriol, glucose, fructose, lactore, and erythritan.

Peptide Aldehydes:

Peptide aldehydes (component (c)) may be selected from di-, tri- or tetrapeptide aldehydes and aldehyde analogues (either of the form B1-BO—R wherein, R is H, $CH_3$, $CX_3$, $CHX_2$, or $CH_2X$ (X=halogen), BO is a single amino acid residue (in one embodiment with an optionally substituted aliphatic or aromatic side chain); and B1 consists of one or more amino acid residues (in one embodiment one, two or three), optionally comprising an N-terminal protection group, or as described in WO 09/118375 and WO 98/13459, or a protease inhibitor of the protein type such as RASI, BASI, WASI (bifunctional alpha-amylase/subtilisin inhibitors of rice, barley and wheat) or $Cl_2$ or SSI.

Other Stabilizers.

Other stabilizers (component (c)) may be selected from salts like NaCl or KCl, and alkali salts of lactic acid and formic acid.

Other stabilizers (component (c)) may be selected from water-soluble sources of zinc (11), calcium (11) and/or magnesium (11) ions in the finished compositions that provide such ions to the enzymes, as well as other metal ions (e.g. barium (11), scandium (11), iron (11), manganese (11), aluminum (111), Tin (11), cobalt (11), copper (11), Nickel (11), and oxovanadium (IV)).

Compounds Stabilizing the Liquid Enzyme Preparation as Such

Compounds stabilizing the liquid enzyme preparation as such means any compound except enzyme stabilizers needed to establish storage stability of a liquid preparation in amounts effective to ensure the storage stability.

Storage stability in the context of liquid preparations to those skilled in the art usually includes aspects of appearance of the product and uniformity of dosage.

Appearance of the product is influenced by the pH of the product and by the presence of compounds such as preservatives, antioxidants, viscosity modifiers, emulsifiers etc.

Uniformity of dosage is usually related to the homogeneity of a product.

Preservatives:

The liquid enzyme preparation of the invention may comprise at least one preservative. Preservatives are added in amounts effective in preventing microbial contamination of the liquid enzyme preparation, preferably the aqueous enzyme preparation.

Non-limiting examples of suitable preservatives include (quaternary) ammonium compounds, isothiazolinones, organic acids, and formaldehyde releasing agents. Non-limiting examples of suitable (quaternary) ammonium compounds include benzalkonium chlorides, polyhexamethylene biguanide (PHMB), Didecyldimethylammonium chloride (DDAC), and N-(3-aminopropyl)-N-dodecylpropane-1,3-diamine (Diamine). Non-limiting examples of suitable isothiazolinones include 1,2-benzisothiazolin-3-one (BIT), 2-methyl-2H-isothiazol-3-one (MIT), 5-chloro-2-methyl-2H-isothiazol-3-one (CIT), 2-octyl-2H-isothiazol-3-one (OIT), and 2-butyl-benzo[d]isothiazol-3-one (BBIT). Non-limiting examples of suitable organic acids include benzoic acid, sorbic acid, L-(+)-lactic acid, formic acid, and salicylic acid. Non-limiting examples of suitable formaldehyde releasing agent include N,N'-methylenebismorpholine (MBM), 2,2',2"-(hexahydro-1,3,5-triazine-1,3,5-triyl)triethanol (HHT), (ethylenedioxy)dimethanol, .alpha., .alpha.', .alpha."-trimethyl-1,3,5-triazine-1,3,5(2H,4H,6H)-triethanol (HPT), 3,3'-methylenebis[5-methyloxazolidine](MBO), and cis-1-(3-chloroallyl)-3,5,7-triaza-1-azoniaadamantane chloride (CTAC).

Further useful preservatives include iodopropynyl butylcarbamate (IPBC), halogen releasing compounds such as dichloro-dimethyl-hydantoine (DCDMH), bromo-chloro-dimethyl-hydantoine (BCDMH), and dibromo-dimethyl-hydantoine (DBDMH); bromo-nitro compounds such as Bronopol (2-bromo-2-nitropropane-1,3-diol), 2,2-dibromo-2-cyanoacetamide (DBNPA); aldehydes such as glutaraldehyde; phenoxyethanol; Biphenyl-2-ol; and zinc or sodium pyrithione.

Surfactants:

The liquid enzyme preparation of the invention may comprise at least one surfactant (component (c)). Examples of surfactants include non-ionic surfactants, amphoteric surfactants, anionic surfactants, and cationic surfactants, hereinafter also referred to as non-ionic surfactants (component (c)), amphoteric surfactants (component (c)), anionic surfactants (component (c)), and cationic surfactants (component (c)). In one embodiment, the liquid enzyme preparation of the invention comprises at least one surfactant selected from non-ionic surfactants, from amphoteric surfactants, and anionic surfactants.

The liquid enzyme preparation may contain 0.1 to 60% by weight relative to the total weight of the enzyme preparation of surfactant (component (c)). Component (c) may comprise at least one compound selected from anionic surfactants, non-ionic surfactants, amphoteric surfactants, and amine oxide surfactants as well as combinations of at least two of the foregoing. In one embodiment, the enzyme preparation of the invention contains 5 to 30% by weight of anionic surfactant and at least one non-ionic surfactant, for example in the range of from 3 to 20% by weight, all relative to the total weight of the enzyme preparation.

At least one non-ionic surfactant (component (c)) may be selected from alkoxylated alcohols, di- and multiblock copolymers of ethylene oxide and propylene oxide and reaction products of sorbitan with ethylene oxide or propylene oxide, alkyl polyglycosides (APG), hydroxyalkyl mixed ethers and amine oxides.

Preferred examples of alkoxylated alcohols and alkoxylated fatty alcohols are, for example, compounds of the general formula (IV)

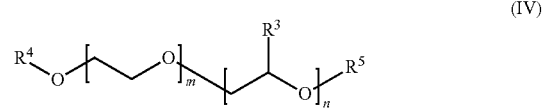

wherein $R^3$ is identical or different and selected from hydrogen and linear $C_1$-$C_{10}$-alkyl, preferably in each case identical and ethyl and particularly preferably hydrogen or methyl, $R^4$ is selected from $C_8$-$C_{22}$-alkyl, branched or linear, for example n-$C_8H_{17}$, n-$C_{10}H_{21}$, n-$C_{12}H_{25}$, n-$C_{14}H_{29}$, n-$C_{16}H_{33}$ or n-$C_{18}H_{37}$, $R^5$ is selected from $C_1$-$C_{10}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl or iso-decyl.

The variables m and n are in the range from zero to 300, where the sum of n and m is at least one, preferably in the range of from 3 to 50. Preferably, m is in the range from 1 to 100 and n is in the range from 0 to 30.

In one embodiment, compounds of the general formula (III) may be block copolymers or random copolymers, preference being given to block copolymers.

Other preferred examples of alkoxylated alcohols are, for example, compounds of the general formula (V):

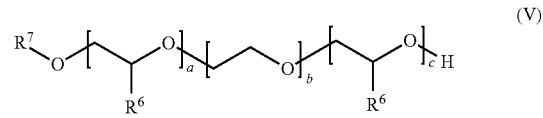

wherein $R^6$ is identical or different and selected from hydrogen and linear $C_1$-$C_{10}$-alkyl, preferably identical in each case and ethyl and particularly preferably hydrogen or methyl, $R^7$ is selected from $C_6$-$C_{20}$-alkyl, branched or linear, in particular n-$C_8H_{17}$, n-$C_{10}H_{21}$, n-$C_{12}H_{25}$, n-$C_{13}H_{27}$, n-$C_{15}H_{31}$, n-$C_{14}H_{29}$, n-$C_{16}H_{33}$, n-$C_{18}H_{37}$, a is a number in the range from zero to 10, preferably from 1 to 6, b is a number in the range from 1 to 80, preferably from 4 to 20, c is a number in the range from zero to 50, preferably 4 to 25.

The sum a+b+c is preferably in the range of from 5 to 100, even more preferably in the range of from 9 to 50.

Preferred examples for hydroxyalkyl mixed ethers are compounds of the general formula (VI)

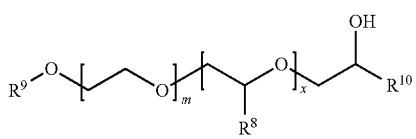

(VI)

in which the variables are defined as follows:

$R^8$ is identical or different and selected from hydrogen and linear $C_1$-$C_{10}$-alkyl, preferably in each case identical and ethyl and particularly preferably hydrogen or methyl, $R^9$ is selected from $C_8$-$C_{22}$-alkyl, branched or linear, for example iso-$C_{11}H_{23}$, iso-$C_{13}H_{27}$, n-$C_8H_{17}$, n-$C_{10}H_{21}$, n-$C_{12}H_{25}$, n-$C_{14}H_{29}$, n-$C_{16}H_{33}$ or n-$C_{18}H_{37}$, $R^{10}$ is selected from $C_1$-$C_{18}$-alkyl, methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, 2-ethylhexyl, n-nonyl, n-decyl, isodecyl, n-dodecyl, n-tetradecyl, n-hexadecyl, and n-octadecyl.

The variables m and x are in the range from zero to 300, where the sum of n and m is at least one, preferably in the range of from 5 to 50. Preferably, m is in the range from 1 to 100 and n is in the range from 0 to 30.

Compounds of the general formulae (V) and (VI) may be block copolymers or random copolymers, preference being given to block copolymers.

Further suitable non-ionic surfactants are selected from di- and multiblock copolymers, composed of ethylene oxide and propylene oxide. Further suitable nonionic surfactants are selected from ethoxylated or propoxylated sorbitan esters. Amine oxides or alkyl polyglycosides, especially linear $C_4$-$C_{18}$-alkyl polyglucosides and branched $C_8$-$C_{18}$-alkyl polyglycosides such as compounds of general average formula (VII) are likewise suitable.

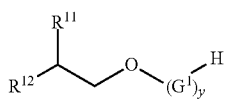

(VII)

wherein:

$R^{11}$ is $C_1$-$C_4$-alkyl, in particular ethyl, n-propyl or isopropyl, $R^{12}$ is —$(CH_2)_2$—$R^{11}$, $G^1$ is selected from monosaccharides with 4 to 6 carbon atoms, especially from glucose and xylose, y in the range of from 1.1 to 4, y being an average number.

Further examples of non-ionic surfactants are compounds of general formula (VIIIa) and (VIIIb)

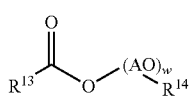

(VIIIa)

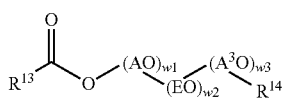

(VIIIb)

wherein

AO is selected from ethylene oxide, propylene oxide and butylene oxide,

EO is ethylene oxide, $CH_2CH_2$—O, $R^{13}$ is $C_1$-$C_4$-alkyl, in particular ethyl, n-propyl or isopropyl, $R^{14}$ selected from $C_8$-$C_{18}$-alkyl, branched or linear $A^3O$ is selected from propylene oxide and butylene oxide, w is a number in the range of from 15 to 70, preferably 30 to 50, w1 and w3 are numbers in the range of from 1 to 5, and w2 is a number in the range of from 13 to 35.

An overview of suitable further non-ionic surfactants can be found in EP-A 0 851 023 and in DE-A 198 19 187.

In one embodiment, the enzyme preparation contains mixtures of two or more different non-ionic surfactants (component (c)).

At least one amphoteric surfactant (component (c)) may be selected from surfactants that bear a positive and a negative charge in the same molecule under use conditions. Preferred examples of amphoteric surfactants are so-called betaine-surfactants. Many examples of betaine-surfactants bear one quaternized nitrogen atom and one carboxylic acid group per molecule. A particularly preferred example of amphoteric surfactants is cocamidopropyl betaine (lauramidopropyl betaine).

Examples of amine oxide surfactants are compounds of the general formula (IX)

$$R^{13}R^{14}R^{15}N \rightarrow O \qquad (IX)$$

wherein $R^{13}$, $R^{14}$ and $R^{15}$ are selected independently from each other from aliphatic, cycloaliphatic or $C_2$-$C_4$-alkylene $C_{10}$-$C_{20}$-alkylamido moieties. Preferably, $R^{12}$ is selected from $C_8$-$C_{20}$-alkyl or $C_2$-$C_4$-alkylene $C_{10}$-$C_{20}$-alkylamido and $R^{13}$ and $R^{14}$ are both methyl.

A particularly preferred example is lauryl dimethyl aminoxide, sometimes also called lauramine oxide. A further particularly preferred example is cocamidylpropyl dimethylaminoxide, sometimes also called cocamidopropylamine oxide.

At least one anionic surfactant (component (c)) may be selected from alkali metal and ammonium salts of $C_8$-$C_{18}$-alkyl sulfates, of $C_8$-$C_{18}$-fatty alcohol polyether sulfates, of sulfuric acid half-esters of ethoxylated $C_4$-$C_{12}$-alkylphenols (ethoxylation: 1 to 50 mol of ethylene oxide/mol), $C_{12}$-$C_{18}$ sulfo fatty acid alkyl esters, for example of $C_{12}$-$C_{18}$ sulfo fatty acid methyl esters, furthermore of $C_{12}$-$C_{18}$-alkylsulfonic acids and of $C_{10}$-$C_{18}$-alkylarylsulfonic acids. Preference is given to the alkali metal salts of the aforementioned compounds, particularly preferably the sodium salts.

Specific examples of anionic surfactants (component (c)) are compounds according to general formula (X)

$$C_sH_{2s+1}\text{—}O(CH_2CH_2O)_t\text{—}SO_3M \qquad (X)$$

wherein s being a number in the range of from 10 to 18, preferably 12 to 14, and even more preferably s=12, t being a number in the range of from 1 to 5, preferably 2 to 4 and even more preferably 3.

M being selected from alkali metals, preferably potassium and even more preferably sodium.

The variables s and t may be average numbers and therefore they are not necessarily whole numbers, while in individual molecules according to formula (X), both s and t denote whole numbers.

Further examples for suitable anionic surfactants (component (c)) are soaps, for example the sodium or potassium salts of stearic acid, oleic acid, palmitic acid, ether carboxylates, and alkylether phosphates.

In one embodiment, the inventive enzyme preparation is aqueous, containing water in amounts in the range of 5% to 95% by weight, in the range of 5% to 30% by weight, in the range of 5% to 25% by weight, or in the range of 20% to 70% by weight, all relative to the total weight of the enzyme preparation. Said enzyme preparation may contain organic solvents in amounts in the range of 0% to 20% by weight relative to the total weight of the enzyme preparation. In one embodiment, the enzyme preparation contains water in amounts in the range of 5% to 15% by weight and no significant amounts of organic solvent, for example 1% by weight or less, all relative to the total weight of the enzyme preparation.

Inventive enzyme preparations may be alkaline or exhibit a neutral or slightly acidic pH value, for example 6 to 14, 6.5 to 13, 8 to 10.5, or 8.5 to 9.0.

Preparation of Enzyme Formulation:

The invention relates to a process for making an enzyme preparation, said process comprising the step of mixing at least component (a) as disclosed above and component (b) as disclosed above.

Component (b) may be solid. Solid component (b) may be added to solid component (a) prior to contact of both with at least one solvent. At least one solvent is as disclosed above. Contact with at least one solvent may result in solubilizing of at least one molecule component (a) and at least one molecule component (b), resulting in stabilization of at least one molecule component (b). In one embodiment, solid components (a) and (b) are completely dissolved in at least one solvent without phase separation.

Solid component (a) may be dissolved in at least one solvent prior to mixing with solid or liquid component (b). In one embodiment, component (a) is completely dissolved in at least one solvent prior to mixing with component (b). At least one solvent is as disclosed above.

Component (b) may be liquid, wherein at least one enzyme may be comprised in a liquid enzyme concentrate as disclosed above. Liquid component (b) may be supplemented with solid component (a), wherein solid component (a) dissolves in liquid component (b). In one embodiment, liquid component (b) is aqueous, preferably resulting from fermentation.

In one embodiment, component (c) as disclosed above is mixed with components (a) and (b), wherein the mixing is characterized in being done in one or more steps.

Enzyme Stabilization

The invention relates to a method of stabilizing component (b) by the step of adding component (a), wherein components (a) and (b) are those disclosed above. In one embodiment, component (b) is liquid. In one embodiment, the invention relates to a method of stabilizing component (b) in the presence of at least one surfactant by the step of adding component (a), wherein components (a) and (b) and at least one surfactant are those disclosed above. In one embodiment, the invention relates to a method of stabilizing component (b) by the step of adding component (a), wherein component (b) comprises at least one lipase and at least one protease.

The invention further relates to a method of stabilizing at least on enzyme in liquid formulations comprising the mixing in no specified order in one or more steps components (a) and (b) as disclosed above with one or more formulation components. In one embodiment, liquid formulations are detergent formulations.

The invention relates to the use of component (a) as additive for component (b). In one embodiment, components (a) and (b) are solid, and component (b) is stabilized when contacting the mixture of the solid components (a) and (b) with at least one solvent. At least one solvent is as disclosed above. Contact with at least one solvent may result in solubilizing of at least one molecule component (a) and at least one molecule component (b), resulting in stabilization of at least one molecule component (b). In one embodiment, solid components (a) and (b) are completely dissolved in at least one solvent without phase separation.

Stabilization of an enzyme may relate to stability in the course of time (e.g. storage stability), thermal stability, pH stability, and chemical stability. The term "enzyme stability" herein preferably relates to the retention of enzymatic activity as a function of time e.g. during storage or operation. The term "storage" herein means to indicate the fact of products or compositions being stored from the time of being manufactured to the point in time of being used in final application. Retention of enzymatic activity as a function of time during storage is called "storage stability".

To determine changes in enzymatic activity over time, the "initial enzymatic activity" of an enzyme may be measured under defined conditions at time zero (i.e. before storage) and the "enzymatic activity after storage" may be measured at a certain point in time later (i.e. after storage).

The enzymatic activity after storage divided by the initial enzymatic activity multiplied by 100 gives the "enzymatic activity available in application" (a %).

An enzyme is stable according to the invention, when its enzymatic activity "available in application" equals 100% when compared to the initial enzymatic activity before storage. An enzyme may be called stable within this invention if its enzymatic activity available in application is at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% when compared to the initial enzymatic activity before storage.

In one embodiment, lipolytic activity available after storage at 37° C. for 30 days is at least 60% when compared to the initial lipolytic activity before storage.

Subtracting a % from 100% gives the "loss of enzymatic activity during storage" when compared to the initial enzymatic activity before storage. In one embodiment, an enzyme is stable according to the invention when essentially no loss of enzymatic activity occurs during storage, i.e. loss in enzymatic activity equals 0% when compared to the initial enzymatic activity before storage. Essentially no loss of enzymatic activity within this invention may mean that the loss of enzymatic activity is less than 30%, less than 25%, less than 20%, less than 15%, less than 10%, less than 9%, less than 8%, less than 7%, less than 6%, less than 5%, less than 4%, less than 3%, less than 2%, or less than 1% when compared to the initial enzymatic activity before storage.

In one embodiment, the loss of lipolytic activity after storage at 37° C. for 30 days is less than 40% when compared to the initial lipolytic activity before storage.

In one aspect of the invention component (a) is used to reduce loss of enzymatic activity during storage of at least one enzyme comprised in a liquid enzyme concentrate. Reduced loss of enzymatic activity within this invention may mean that the loss of enzymatic activity is reduced by at least 5%, by at least 10%, by at least 15%, by at least 20%, by at least 25%, by at least 30%, by at least 40%, by at least 50%, by least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 99.5% when compared to the initial enzymatic activity before storage.

In one embodiment, the loss of lipolytic activity after storage at 37° C. for 30 days is reduced by component (a) by at least 60% when compared to the initial lipolytic activity before storage.

In one embodiment, the loss of proteolytic activity after storage at 37° C. for 30 days is reduced by component (a) by at least 20% when compared to the initial proteolytic activity before storage.

Enzymes inhibited by an enzyme inhibitor usually exhibit reduced enzymatic activity when compared to the uninhibited enzymatic activity of said enzyme. The enzymatic activity measured after adding enzyme inhibitor divided by the initial enzymatic activity multiplied by 100 may be called "residual enzymatic activity" (b %) herein. Enzymes may be called "stabilized" herein when they exhibit residual enzymatic activity (b %) which is less than 50%, less than 45%, less than 40%, less than 35%, less than 30%, less than 25%, less than 20%, less than 15%, less than 10%, less than 5%, or less than 1% when compared to the initial enzymatic activity before storage. An enzyme may be called stabilized, if its enzymatic activity available in application after release of an inhibitor is at least 70%, at least 75%, at least 80%, at least 85%, at least 90%, at least 91%, at least 92%, at least 93%, at least 94%, at least 95%, at least 96%, at least 97%, at least 98%, at least 99%, at least 99.5%, or 100% when compared to the initial enzymatic activity before storage. The inhibitor may be called "enzyme stabilizer" herein.

Use of Enzyme Preparation for Formulation Processes

The invention in one aspect relates to the use of the liquid enzyme preparation of the invention to be formulated into detergent formulations, wherein components (a) and (b) are mixed in no specified order in one or more steps with one or more detergent components.

In one aspect of the invention relates to a detergent formulation containing the liquid enzyme preparation of the invention and one or more detergent components.

Detergent components vary in type and/or amount in a detergent formulation depending on the desired application such as laundering white textiles, colored textiles, and wool. The component(s) chosen further depend on physical form of a detergent formulation (liquid, solid, gel, provided in pouches or as a tablet, etc). The component(s) chosen e.g. for laundering formulations further depend on regional conventions which themselves are related to aspects like washing temperatures used, mechanics of laundry machine (vertical vs. horizontal axis machines), water consumption per wash cycle etc. and geographical characteristics like average hardness of water.

Individual detergent components and usage in detergent formulations are known to those skilled in the art. Suitable detergent components comprise inter alia surfactants, builders, polymers, alkaline, bleaching systems, fluorescent whitening agents, suds suppressors and stabilizers, hydrotropes, and corrosion inhibitors. Further examples are described e.g. in "complete Technology Book on Detergents with Formulations (Detergent Cake, Dishwashing Detergents, Liquid & Paste Detergents, Enzyme Detergents, Cleaning Powder & Spray Dried Washing Powder)", Engineers India Research Institute (EIRI), 6$^{th}$ edition (2015). Another reference book for those skilled in the art may be "Detergent Formulations Encyclopedia", Solverchem Publications, 2016.

It is understood that the detergent components are in addition to the components comprised in the enzyme preparation of the invention. If a component comprised in the enzyme preparation of the invention is also a detergent component, it might be the concentrations that need to be adjusted that the component is effective for the purpose desired in the detergent formulation.

Detergent components may have more than one function in the final application of a detergent formulation, therefore any detergent component mentioned in the context of a specific function herein, may also have another function in the final application of a detergent formulation. The function of a specific detergent component in the final application of a detergent formulation usually depends on its amount within the detergent formulation, i.e. the effective amount of a detergent component.

The term "effective amount" includes amounts of individual components to provide effective stain removal and/or effective cleaning conditions (e.g. pH, quantity of foaming), amounts of certain components to effectively provide optical benefits (e.g. optical brightening, dye transfer inhibition), and/or amounts of certain components to effectively aid the processing (maintain physical characteristics during processing, storage and use; e.g. rheology modifiers, hydrotropes, desiccants).

In one embodiment, a detergent formulation is a formulation of more than two detergent components, wherein at least one component is effective in stain-removal, at least one component is effective in providing the optimal cleaning conditions, and at least one component is effective in maintaining the physical characteristics of the detergent.

Detergent formulations of the invention may comprise component (a) and component (b) being dissolved in solvent. Dissolved may mean being dissolved in the overall detergent formulation. Dissolved may mean component (a) and component (b) being part of the liquid enzyme preparation of the invention which may be encapsulated. Encapsulated liquid enzyme preparation may be part of a liquid detergent formulation or part of a solid detergent formulation.

In one embodiment of the present invention, detergent formulations contain 0.5 to 20% by weight, particularly 1-10% by weigh component (b) and 0.01% to 10% of component (a), more particularly 0.05 to 5% by weight and most particularly 0.1% to 2% by weight of component (a), all relative to the total weight of the liquid detergent formulation.

Detergent formulations of the invention may comprise at least one compound selected from builders, polymers, fragrances and dyestuffs.

In one embodiment of the present invention component (a) is used as a builder in detergent formulations in amounts effective to provide the desired builder function. Using component (a) as builder allows flexible detergent formulation, either with high or low water content. For liquid detergent formulations with low water content, no further builder substances besides component (a) may be used. Low water content herein may mean at least ≤30% by weight, at least ≤20% by weight, at least ≤10% by weight, or at least ≤5% by weight, all relative to the total weight of the detergent formulation.

In one embodiment, detergent formulations may contain one or more builders different from component (a).

Inventive detergent formulations may contain 1 to 40% by weight of a detergent builder different from component (a), such as, but not limited to zeolite, phosphate, phosphonate, citrate, polymer builders, or aminocarboxylates such as the alkali metal salts of iminodisuccinates, for example IDS-Na$_4$, furthermore nitrilotriacetic acid ("NTA"), methylglycine diacetic acid ("MGDA"), glutamic acid diacetic acid ("GLDA"), ethylene diamine tetraacetic acid ("EDTA") or diethylene-triamine pentaacetic acid ("DTPA"). Preferred alkali metal salts are the potassium salts and especially the sodium salts.

Further examples of detergent builders are polymers with complexing groups like, for example, polyethylenimine in which 20 to 90 mole-% of the N-atoms bear at least one CH$_2$COO— group, and the respective alkali metal salts of the above sequestrants, especially their sodium salts.

Further examples of suitable polymers are polyalkylenimines, for example polyethylenimines and polypropylene imines. Polyalkylenimines may be used as such or as polyalkoxylated derivatives, for examples ethoxylated or propoxylated. Polyalkylenimines contain at least three alkylenimine units per molecule.

In one embodiment of the present invention, said alkylenimine unit is a C$_2$-C$_{10}$-alkylendiamine unit, for example a 1,2-propylendiamine, preferably an α,ω-C$_2$-C$_{10}$-alkylendiamine, for example 1,2-ethylendiamine, 1,3-propylendiamine, 1,4-butylendiamine, 1,5-pentylendiamine, 1,6-hexandiamine (also being referred to as 1,6-hexylendiamine), 1,8-diamine or 1,10-decandiamine, even more preferred are 1,2-ethylendiamine, 1,3-propylendiamine, 1,4-butylendiamine, and 1,6-hexandiamine.

In another embodiment of the present invention, said polyalkylenimine is selected from polyalkylenimine unit, preferably a polyethylenimine or polypropylenimine unit.

The term "polyethylenimine" in the context of the present invention does not only refer to polyethylenimine homopolymers but also to polyalkylenimines containing NH—CH$_2$—CH$_2$—NH structural elements together with other alkylene diamine structural elements, for example NH—CH$_2$—CH$_2$—CH$_2$—NH structural elements, NH—CH$_2$—CH(CH$_3$)—NH structural elements, NH—(CH$_2$)$_4$—NH structural elements, NH—(CH$_2$)$_6$—NH structural elements or (NH—(CH$_2$)$_8$—NH structural elements but the NH—CH$_2$—CH$_2$—NH structural elements being in the majority with respect to the molar share. Preferred polyethylenimines contain NH—CH$_2$—CH$_2$—NH structural elements being in the majority with respect to the molar share, for example amounting to 60 mol-% or more, preferably amounting to at least 70 mol-%, referring to all alkylenimine structural elements. In a special embodiment, the term polyethylenimine refers to those polyalkylenimines that bear only one or zero alkylenimine structural element per polyethylenimine unit that is different from NH—CH$_2$—CH$_2$—NH.

The term "polypropylenimine" in the context of the present invention does not only refer to polypropyleneimine homopolymers but also to polyalkylenimines containing NH—CH$_2$—CH(CH$_3$)—NH structural elements together with other alkylene diamine structural elements, for example NH—CH$_2$—CH$_2$—CH$_2$—NH structural elements, NH—CH$_2$—CH$_2$—NH structural elements, NH—(CH$_2$)$_4$—NH structural elements, NH—(CH$_2$)$_6$—NH structural elements or (NH—(CH$_2$)$_8$—NH structural elements but the NH—CH$_2$—CH(CH$_3$)—NH structural elements being in the majority with respect to the molar share. Preferred polypropylenimines contain NH—CH$_2$—CH(CH$_3$)—NH structural elements being in the majority with respect to the molar share, for example amounting to 60 mol-% or more, more preferably amounting to at least 70 mol-%, referring to all alkylenimine structural elements. In a special embodiment, the term polypropylenimine refers to those polyalkylenimines that bear only one or zero alkylenimine structural element per polypropylenimine unit that is different from NH—CH$_2$—CH(CH$_3$)—NH.

Branches may be alkylenamino groups such as, but not limited to —CH$_2$—CH$_2$—NH$_2$ groups or (CH$_2$)$_3$—NH$_2$— groups. Longer branches may be, for examples, —(CH$_2$)$_3$—N(CH$_2$CH$_2$CH$_2$NH$_2$)$_2$ or —(CH$_2$)$_2$—N(CH$_2$CH$_2$NH$_2$)$_2$ groups. Highly branched polyethylenimines are, e.g., polyethylenimine dendrimers or related molecules with a degree of branching in the range from 0.25 to 0.95, preferably in the range from 0.30 to 0.80 and particularly preferably at least 0.5. The degree of branching can be determined for example by $^{13}$C-NMR or $^{15}$N-NMR spectroscopy, preferably in D$_2$O, and is defined as follows:

$$DB=D+T/D+T+L$$

with D (dendritic) corresponding to the fraction of tertiary amino groups, L (linear) corresponding to the fraction of secondary amino groups and T (terminal) corresponding to the fraction of primary amino groups.

Within the context of the present invention, branched polyethylenimine units are polyethylenimine units with DB in the range from 0.25 to 0.95, particularly preferably in the range from 0.30 to 0.90 and very particularly preferably at least 0.5. Preferred polyethylenimine units are those that exhibit little or no branching, thus predominantly linear or linear polyethylenimine units.

In the context of the present invention, CH$_3$— groups are not being considered as branches.

In one embodiment of the present invention polyalkylenimine may have a primary amine value in the range of from 1 to 1000 mg KOH/g, preferably from 10 to 500 mg KOH/g, most preferred from 50 to 300 mg KOH/g. The primary amine value can be determined according to ASTM D2074-07.

In one embodiment of the present invention polyalkylenimine may have a secondary amine value in the range of from 10 to 1000 mg KOH/g, preferably from 50 to 500 mg KOH/g, most preferred from 50 to 500 mg KOH/g. The secondary amine value can be determined according to ASTM D2074-07.

In one embodiment of the present invention polyalkylenimine may have a tertiary amine value in the range of from 1 to 300 mg KOH/g, preferably from 5 to 200 mg KOH/g, most preferred from 10 to 100 mg KOH/g. The tertiary amine value can be determined according to ASTM D2074-07.

In one embodiment of the present invention, the molar share of tertiary N atoms is determined by $^{15}$N-NMR spectroscopy. In cases that tertiary amine value and result according to $^{13}$C-NMR spectroscopy are inconsistent, the results obtained by $^{13}$C-NMR spectroscopy will be given preference.

In one embodiment of the present invention, the average molecular weight M$_w$ of said polyalkylenimine is in the range of from 250 to 100,000 g/mol, preferably up to 50,000 g/mol and more preferably from 800 up to 25,000 g/mol. The average molecular weight M$_w$ of polyalkylenimine may be determined by gel permeation chromatography (GPC) of the intermediate respective polyalkylenimine, with 1.5% by weight aqueous formic acid as eluent and cross-linked polyhydroxyethyl methacrylate as stationary phase.

Said polyalkylenimine may be free or alkoxylated, said alkoxylation being selected from ethoxylation, propoxylation, butoxylation and combinations of at least two of the foregoing. Preference is given to ethylene oxide, 1,2-propylene oxide and mixtures of ethylene oxide and 1,2- propylene oxide. If mixtures of at least two alkylene oxides are applied, they can be reacted step-wise or simultaneously.

In one embodiment of the present invention, an alkoxylated polyalkylenimine bears at least 6 nitrogen atoms per unit.

In one embodiment of the present invention, polyalkylenimine is alkoxylated with 2 to 50 moles of alkylene oxide per NH group, preferably 5 to 30 moles of alkylene oxide per NH group, even more preferred 5 to 25 moles of ethylene oxide or 1,2-propylene oxide or combinations therefrom per NH group. In the context of the present invention, an $NH_2$ unit is counted as two NH groups. Preferably, all—or almost all—NH groups are alkoxylated, and there are no detectable amounts of NH groups left.

Depending on the manufacture of such alkoxylated polyalkylenimine, the molecular weight distribution may be narrow or broad. For example, the polydispersity $Q=M_w/M_n$ in the range of from 1 to 3, preferably at least 2, or it may be greater than 3 and up to 20, for example 3.5 to 15 and even more preferred in the range of from 4 to 5.5.

In one embodiment of the present invention, the polydispersity Q of alkoxylated polyalkylenimine is in the range of from 2 to 10.

In one embodiment of the present invention alkoxylated polyalkylenimine is selected from polyethoxylated polyethylenimine, ethoxylated polypropylenimine, ethoxylated α,ω-hexandiamines, ethoxylated and propoxylated polyethylenimine, ethoxylated and propoxylated polypropylenimine, and ethoxylated and poly-propoxylated α,ω-hexandiamines.

In one embodiment of the present invention the average molecular weight $M_n$ (number average) of alkoxylated polyethylenimine is in the range of from 2,500 to 1,500,000 g/mol, determined by GPC, preferably up to 500,000 g/mol.

In one embodiment of the present invention, the average alkoxylated polyalkylenimine are selected from ethoxylated α,ω-hexanediamines and ethoxylated and poly-propoxylated α,ω-hexanediamines, each with an average molecular weight $M_n$ (number average) in the range of from 800 to 500,000 g/mol.

Examples of buffers are monoethanolamine and N,N,N-triethanolamine.

Examples of defoamers are silicones.

Examples of fragrances are benzyl salicylate, 2-(4-tert.-butylphenyl) 2-methylpropional, commercially available as Lilial®, and hexyl cinnamaldehyde.

Examples of dyestuffs are Acid Blue 9, Acid Yellow 3, Acid Yellow 23, Acid Yellow 73, Pigment Yellow 101, Acid Green 1, Solvent Green 7, and Acid Green 25.

Liquid detergent formulations may comprise at least one compound selected from organic solvents, preservatives, viscosity modifiers, and hydrotropes.

In one embodiment of the present invention, liquid detergent formulations contain amounts of organic solvents are 0.5 to 25% by weight, relative to the total weight of the liquid detergent formulation. Especially when inventive liquid detergent formulations are provided in pouches or the like, 8 to 25% by weight of organic solvent(s) relative to the total weight of the liquid detergent formulation may be contained. Organic solvents are those disclosed above.

Inventive liquid detergent formulations may contain one or more preservatives selected from those disclosed above in amounts effective in avoiding microbial contamination of the liquid detergent formulation.

In one embodiment of the present invention, liquid detergent formulations contain one or more viscosity modifiers. Non-limiting examples of suitable viscosity modifiers include agar-agar, carragene, tragacanth, gum arabic, alginates, pectins, hydroxyethyl cellulose, hydroxypropyl cellulose, starch, gelatin, locust bean gum, cross-linked poly (meth)acrlyates, for example polyacrlyic acid cross-linked with bis-(meth)acrylamide, furthermore silicic acid, clay such as—but not limited to—montmorrilionite, zeolite, dextrin, and casein. Viscosity modifiers may be contained in amounts effective in providing the desired viscosity.

In one embodiment of the present invention, liquid detergent formulations contain one or more hydrotropes which may be organic solvents such as ethanol, isopropanol, ethylene glycol, 1,2-propylene glycol, and further organic solvents that are water-miscible under normal conditions without limitation. Further examples of suitable hydrotropes are the sodium salts of toluene sulfonic acid, of xylene sulfonic acid, and of cumene sulfonic acid. Hydrotropes may be contained in amounts that facilitate or enables the dissolution of compounds that exhibit limited solubility in water.

"Detergent formulation" or "cleaning formulation" herein means formulations designated for cleaning soiled material. Cleaning includes laundering and hard surface cleaning. Soiled material according to the invention includes textiles and/or hard surfaces.

The term "laundering" relates to both household laundering and industrial laundering and means the process of treating textiles with a solution containing a detergent formulation of the present invention. The laundering process may be carried out by using technical devices such as a household or an industrial washing machine. Alternatively, the laundering process may be done by hand.

The term "textile" means any textile material including yarns (thread made of natural or synthetic fibers used for knitting or weaving), yarn intermediates, fibers, non-woven materials, natural materials, synthetic materials, as well as fabrics (a textile made by weaving, knitting or felting fibers) made of these materials such as garments (any article of clothing made of textile), cloths and other articles.

The term "fibers" includes natural fibers, synthetic fibers, and mixtures thereof. Examples of natural fibers are of plant (such as flax, jute and cotton) or animal origin, comprising proteins like collagen, keratin and fibroin (e.g. silk, sheeps wool, angora, mohair, cashmere). Examples for fibers of synthetic origin are polyurethane fibers such as Spandex® or Lycra®, polyester fibers, polyolefins such as elastofin, or polyamide fibers such as nylon. Fibers may be single fibers or parts of textiles such as knitwear, wovens, or nonwovens.

The term "hard surface cleaning" is defined herein as cleaning of hard surfaces wherein hard surfaces may include any hard surfaces in the household, such as floors, furnishing, walls, sanitary ceramics, glass, metallic surfaces including cutlery or dishes.

The term "dish wash" refers to all forms of washing dishes, e.g. by hand or automatic dish wash. Dish washing includes, but is not limited to, the cleaning of all forms of crockery such as plates, cups, glasses, bowls, all forms of cutlery such as spoons, knives, forks and serving utensils as well as ceramics, plastics such as melamine, metals, china, glass and acrylics.

Further Use

The invention relates to a method for removing stains comprising the steps of contacting a stain with a detergent formulation comprising components (a) and (b) and one or more detergent components. In one embodiment, the detergent formulation comprises the enzyme preparation of the invention. In one embodiment, the method relates to the removal of stains comprising fat.

Fats can be sub-classified as fat, grease or oil depending on the melting temperature. Oil is usually liquid at room temperature. Grease has a higher viscosity than oil at room temperature and may be called pasty.

In one embodiment, removing of stains comprising fat is done at temperatures ≤40° C., is particular at temperatures ≤30° C.

EXAMPLES

The invention will be further illustrated by working examples.

General remarks: percentages are weight percent unless specifically noted otherwise.

Acetylcholine (A.12) was purchased from Sigma Aldrich. The counterion was chloride.

The precursor of (A.14) can be produced directly instead of use of HCl in the ethoxylation of trimethylamine or via reaction of choline hydrogencarbonate with methanesulfonic, see Constantinescu et al in Chem. Eng. Data, 2007, 521280-1285.

I. Synthesis of Salts (Component (a))

Based upon the amounts of water distilled off and by IR spectroscopy it could be shown that the esterification reactions were complete.

90% methanesulfonic acid refers to a mixture from 10% water and 90% methanesulfonic acid.

I.1 Synthesis of Inventive Salt (A.1):

An amount of 225 g (1.5 mole) tartaric acid was dissolved in 280 g of a 75% by weight aqueous solution of choline chloride (1.5 mole). Water was removed within 45 minutes in a rotary evaporator (2-l-flask)-oil bath temperature of 100 to 120° C., 50 to 80 mbar. An amount of 15 g of 90% by weight aqueous methanesulfonic acid were added and the temperature was raised to 145° C. at a pressure of 800 mbar. After one hour of rotary evaporation the pressure was continuously reduced to 10 mbar while water was removed for another 4.5 h at 145° C. A light yellowish substance was obtained that was diluted with 200 g diethylene glycol. An amount of 617 g of a yellowish liquid was obtained. An aliquot of 200 g of the liquid so obtained was neutralized with 7.8 g ethanolamine to a pH value of 6 to 6.5 (10% in water). Inventive salt (A.1) was obtained.

I.2 Synthesis of Inventive Salt (A.2):

An amount of 150 g tartaric acid (1.0 mole) was dissolved in 374 g of a 75% by weight aqueous solution of choline chloride (2.0 mole). Water was removed within 45 minutes in a rotary evaporator (2-l-flask)-oil bath temperature of 100 to 120° C., 50 to 80 mbar. An amount of 15 g of 90% by weight methanesulfonic acid were added and the temperature was raised to 145° C. at a pressure of 800 mbar. After one hour of rotary evaporation the pressure was continuously reduced to 10 mbar while water was removed for another 4.5 h at 145° C. A light yellowish substance was obtained that was diluted with 200 g diethylene glycol. An amount of 607 g of a yellowish liquid were obtained. An aliquot of 200 g of the liquid so obtained was neutralized with 8.7 g ethanolamine to a pH value of 6 to 6.5 (10% in water). Inventive salt (A.2) was obtained.

I.3 Synthesis of Inventive Salt (A.3):

An amount of 210 g citric acid monohydrate (1.0 mole) was dissolved in 374 g of a 75% by weight aqueous solution of choline chloride (2.0 moles). Water was removed within 45 minutes in a rotary evaporator (2-l-flask)-oil bath temperature of 100 to 120° C., 50 to 80 mbar. An amount of 18 g of 90% by weight methanesulfonic acid were added and the temperature was raised to 145° C. at a pressure of 800 mbar. After one hour of rotary evaporation, the pressure was continuously reduced to 10 mbar while water was removed for another 4.5 h at 145° C. A light yellowish substance was obtained that was diluted with 200 g diethylene glycol. An amount of 607 g of a yellowish liquid was obtained. An aliquot of 200 g of the liquid so obtained was neutralized with 10.3 g ethanolamine to a pH value of 6 to 6.5 (10% in water). Inventive salt (A.3) was obtained.

I.4 Synthesis of Inventive Salt (A.4):

An amount of 210 g citric acid monohydrate (1.0 mol) was dissolved in 561 g of a 75% by weight aqueous solution of choline chloride (3.0 moles). Water was removed within 45 minutes in a rotary evaporator (2-l-flask)-oil bath temperature of 100 to 120° C., 50 to 80 mbar. An amount of 18 g of 90% by weight methanesulfonic acid were added and the temperature was raised to 145° C. at a pressure of 800 mbar. After one hour of rotary evaporation the pressure was continuously reduced to 10 mbar while water was removed for another 4.5 h at 145° C. A light yellowish substance was obtained that was diluted with 270 g diethylene glycol. An amount of 868 g of a yellowish liquid was obtained. An aliquot of 200 g of the liquid so obtained was neutralized with 9.6 g ethanolamine to a pH value of 6 to 6.5 (10% in water). Inventive salt (A.4) was obtained.

I.5 Synthesis of Inventive Salt (A.5): An amount of 210 g citric acid monohydrate (1.0 mol) were dissolved in 485 g of a 75% by weight aqueous solution of choline methanesulfonate (2.0 mol). Water was removed within 45 minutes in a rotary evaporator (2-l-flask)-oil bath temperature of 100 to 120° C., 50 to 80 mbar. An amount of 18 g of 90% by weight methanesulfonic acid were added and the temperature was raised to 145° C. at a pressure of 800 mbar. After one hour of rotary evaporation the pressure was continuously reduced to 10 mbar while water was removed for another 4.5 h at 145° C.

A light yellowish substance was obtained that was diluted with 200 g diethylene glycol. An amount of 663 g of a yellowish liquid was obtained. An aliquot of 200 g of the liquid so obtained was neutralized with 12.5 g ethanolamine to a pH value of 6 to 6.5 (10% in water). Inventive salt (A.5) was obtained.

I.6 Synthesis of Inventive Salt (A.6):

An amount of 98.1 g maleic anhydride (1.0 mol) were mixed with 363 g of choline methanesulfonate (2.0 moles) as dry substance. The mixture was heated in a rotary evaporator to 135° C. After one hour of mixing an amount of 12 g of methanesulfonic acid (pure) was added and the temperature was raised to 145° C. at a pressure of 800 mbar. After one hour of mixing the pressure was continuously reduced to 10 mbar while water was removed for another 4.5 h at 145° C. A light yellowish substance was obtained that was diluted with 200 g diethylene glycol. An amount of 653 g of a yellowish liquid was obtained. An aliquot of 200 g of the liquid so obtained was neutralized with 8.9 g ethanolamine to a pH value of 6 to 6.5 (10% in water). Inventive salt (A.6) was obtained.

I.7 Synthesis of Inventive Salt (A.7):

An amount of 210 g citric acid monohydrate (1.0 mole) was dissolved in 437 g of a 70% by weight aqueous solution of beta-methyl choline chloride (HO—CH($CH_3$)—$CH_2$—N($CH_3$)$_3$ Cl, 2.0 moles). Water was removed within 45 minutes in a rotary evaporator (2-l-flask)-oil bath temperature of 100 to 120° C., 50 to 80 mbar. An amount of 18 g of 90% by weight methanesulfonic acid were added and the temperature was raised to 145° C. at a pressure of 800 mbar. After one hour of rotary evaporation the pressure was continuously reduced to 10 mbar while water was removed for another 4.5 h at 145° C. A light yellowish substance was obtained that was diluted with 200 g diethylene glycol. An amount of 676 g of a yellowish liquid was obtained. An aliquot of 200 g of the liquid so obtained was neutralized with 12.3 g ethanolamine to a pH value of 6 to 6.5 (10% in water). Inventive salt (A.7) was obtained.

I.8 Synthesis of Inventive Salt (A.8):

An amount of 105 g citric acid monohydrate (0.5 moles) was dissolved in 327 g of a 70% by weight aqueous solution of beta-methyl choline chloride (1.5 moles). Water was removed within 45 minutes in a rotary evaporator (2-l-flask)-oil bath temperature of 100 to 120° C., 50 to 80 mbar. An amount of 13 g of 90% methanesulfonic acid by weight methanesulfonic acid was added and the temperature was raised to 145° C. at a pressure of 800 mbar. After one hour of rotary evaporation the pressure was continuously reduced to 10 mbar while water was removed for another 4.5 h at 145° C. A light yellowish substance was obtained that was diluted with 170 g diethylene glycol. An amount of 471 g of a yellowish liquid was obtained. An aliquot of 200 g of the liquid so obtained was neutralized with 21.7 g triethanolamine to a pH value of 6 to 6.5 (10% in water). Inventive salt (A.8) was obtained.

I.9 Synthesis of Inventive Salt (A.9):

An amount of 210 g citric acid monohydrate (1.0 mole) was dissolved in 520 g of a 70% by weight aqueous solution of beta-n-propyl choline chloride (2.0 moles). Water was removed within 45 minutes in a rotary evaporator (2-l-flask)-oil bath temperature of 100 to 120° C., 50 to 80 mbar. An amount of 18 g of 90% methanesulfonic acid was added and the temperature was raised to 145° C. at a pressure of 800 mbar. After one hour of rotary evaporation the pressure was continuously reduced to 10 mbar while water was removed for another 4.5 h at 145° C. A light yellowish substance was obtained that was diluted with 250 g propylene glycol. An amount of 774 g of a yellowish liquid was obtained. An aliquot of 200 g of the liquid so obtained was neutralized with 11.9 g ethanolamine to a pH value of 6 to 6.5 (10% in water). Inventive salt (A.9) was obtained.

I.10 Synthesis of Inventive Salt (A.10):

An amount of 210 g citric acid monohydrate (1.0 mole) was dissolved in 520 g of a 70% aqueous solution of dimethylmonobutylcholine chloride (2.0 moles). Water was removed within 45 minutes in a rotary evaporator (2-l-flask)-oil bath temperature of 100 to 120° C., 50 to 80 mbar. An amount of 18 g of 90% methanesulfonic acid was added and the temperature was raised to 145° C. at a pressure of 800 mbar. After one hour of rotary evaporation the pressure was continuously reduced to 10 mbar while water was removed for another 4.5 h at 145° C. A light yellowish substance was obtained that was diluted with 200 g propylene glycol. An amount of 788 g of a yellowish liquid. An aliquot of 200 g of the liquid so obtained was neutralized with 11.4 g ethanolamine to a pH value of 6 to 6.5 (10% in water). Inventive salt (A.10) was obtained.

I.11 Synthesis of Inventive Salt (A.11):

An amount of 105 g citric acid monohydrate (0.5 moles) was dissolved in 397 g of a 60% by weight aqueous solution of dimethyl n-octylcholine chloride (1.0 mole). Water was removed within 90 minutes in a rotary evaporator (2-l-flask)-oil bath temperature of 100 to 120° C., 50 to 80 mbar. An amount of 9.5 g of 90% methanesulfonic acid was added and the temperature was raised to 145° C. at a pressure of 800 mbar. After one hour of rotary evaporation the pressure was continuously reduced to 10 mbar while water was removed for another 4.5 h at 145° C. A light yellowish substance was obtained that was diluted with 200 g propylene glycol. An amount of 470 g of a yellowish liquid was obtained. An aliquot of 200 g of the liquid so obtained was neutralized with 8.9 g ethanolamine to a pH value of 6 to 6.5 (10% in water). Inventive salt (A.11) was obtained.

I.13 Synthesis of Inventive Salt (A.13):

An amount of 85 g gallic acid (3,4,5-trihydroxybenzoic-acid, 0.5 moles) was dispersed in 121 g of a 75% by weight aqueous solution of choline methanesulfonate (0.5 moles). Water was removed within 90 minutes in a rotary evaporator (2-l-flask)-oil bath temperature of 100 to 120° C., 50 to 80 mbar. An amount of 8 g of 90% methanesulfonic acid was added and the temperature was raised to 145° C. at a pressure of 800 mbar. After one hour of rotary evaporation the pressure was continuously reduced to 10 mbar while water was removed for another 4.5 h at 145° C. A light yellowish substance was obtained that was diluted with 100 g diethylene glycol. An amount of 271 g of a yellowish liquid was obtained. An aliquot of 100 g of the liquid so obtained was neutralized with 4.6 g ethanolamine to a pH value of 6 to 6.5 (10% in water). Inventive salt (A.13) was obtained.

Comparative Salts:

C-(A.15): Choline chloride, 75% by weight aqueous solution, commercially available from BASF SE

C-(A.16):

An amount of 75 g (0.5 mol) tartaric acid was portion-wise dissolved (15 g units) in 206 g of an 80% by weight aqueous solution of choline bicarbonate (1.0 mol). The solution was stirred until the $CO_2$ evolution ceased. Water was removed within 90 minutes by rotary evaporation (2-l-flask)-oil bath temperature of 120° C., 10 mbar. A clear substance was obtained that was diluted with 150 g diethylene glycol. 390 g of a clear solution were obtained, C-(A.16). No ester formation could be detected.

C-(A.17): An amount of 105 g (0.5 mol) citric acid monohydrate was portion-wise dissolved (20 g units) in 206 g of an 80% by weight aqueous solution of choline bicarbonate (1.0 mol). The solution was stirred until the $CO_2$ evolution ceased. Water was removed within 90 minutes by rotary evaporation (2-l-flask)-oil bath temperature of 120° C., 10 mbar. A clear substance was obtained that was diluted with 150 g diethylene glycol. 412 g of a clear solution were obtained, C-(A.17). No ester formation could be detected.

C-(A.18): An amount of 105 g (0.5 mol) citric acid monohydrate was portion-wise dissolved (20 g units) in 309 g of an 80% by weight aqueous solution of choline bicarbonate (1.5 moles). The solution was stirred until the $CO_2$ evolution ceased. Water was removed within 90 minutes by rotary evaporation (2-l-flask)-oil bath temperature of 120° C., 10 mbar. A clear substance was obtained that was diluted with 150 g diethylene glycol. 497 g of a clear viscous solution were obtained, C-(A.18). No ester formation could be detected.

C-(A.19): citric acid monohydrate
C-(A.20): monosodium salt of citric acid
C-(A.21): disodium salt of citric acid
C-(A.22): trisodium salt of citric acid
C-(A.19), C-(A.20), C-(A.21) and C-(A.22) are known builder compounds used in detergents formulations.

II. Application Tests

II.1 Liquid Formulations

Low water liquid detergent formulations substitute water with glycols as like diethylene glycol or DPG and hence solubility is inevitable. Salts (A.1) to (A.11) and C-(A.16) to C-(A.18) are each soluble in diethylene glycol and/or dipropylene glycol and hence can be formulated without water.

50 g of C-(A.19), C-(A.20), C-(A.21) and C-(A.22) were each combined in a flask together with 100 g diethylene glycol and heated at 100° C. for 30 minutes under stirring. The heating source was removed and the resulting white suspensions were cooled to ambient temperature over a period of 10 hours. The resulting slurries were filtered (paper filter) and the filter cakes washed twice with 50 g isopropanol. The isolated compounds C-(A.19), C-(A.20), C-(A.21) and C-(A.22) were gravimetrically determined, showing that in the absence of water C-(A.19), C-(A.20), C-(A.21) and C-(A.22) cannot be used due to insufficient solubility. The following amounts were obtained as filter cakes: C-(A.19): 44.0 g; C-(A.20): 45.8 g; C-(A.21): 47.2 g; C-(A.22): 48.2 g.

II.2 Enzyme Stability

The storage stability of Lipase and Protease in water was assessed at 37° C.

Base test formulations were manufactured by making base formulations I to VI by mixing the components according to Table 1.

The respective salt (component (a)) or comparative compound was added, if applicable, to the respective base formulation in amounts as indicated in Table 1.

Enzyme (component (b)) was added, to the respective base formulation in amounts as indicated in Table 1. The amount of enzyme as provided in Table 1 refers to active protein. Either lipase or protease was added, depending on which enzyme activity was measured.

Lipolase® 100 L (CAS-No. 9001-62-1, EC-No. 232-619-9) was purchased from Sigma-Aldrich. Savinase® 16.0 L (CAS-No. 9014-01-1, EC-No. 232-752-2) was purchased from Sigma-Aldrich.

Water was added to accomplish the balance to 100.

TABLE 1 liquid formulations

| | | wt % in formulation | | | | | |
|---|---|---|---|---|---|---|---|
| Ingredients | reference | I. | II. | III. | IV. | V. | VI. |
| Base formulation: | | | | | | | |
| (B.1) | 6 | 15 | 8 | — | 35 | 30 | 25 |
| (B.2) | — | — | 6 | 8 | — | — | — |
| (B.3) | 7.5 | 6 | 4 | — | 8 | — | 22 |
| (B.4) | 2 | 2 | — | — | 10 | 12 | 6 |
| (B.5) | 8 | — | 4 | 8 | 4 | 14 | — |
| (B.6) | — | — | 2.5 | — | — | 5 | — |
| Sorbitol | — | 3 | — | — | 3 | — | — |
| PEI-EO20 | — | 3 | 5 | 3 | 5 | 5 | — |
| Propyleneglycol | — | 8 | 4 | — | 8 | 6 | 4 |
| Glycerol (G) or Ethanol (E) | (E) 2.5 | — | — | (G) 6 | — | (G) 6 | (G) 8 |
| Ca-formiate | — | 1 | — | 1 | 2 | 2 | — |
| Additives: | | | | | | | |
| Savinase 16.0 L | 0.5 | 0.5 | 0.5 | 0.5 | 0.5 | 0.5 | 0.5 |
| Lipolase | 0.4 | 0.4 | 0.4 | 0.4 | 0.4 | 0.4 | 0.4 |
| component (a)** | — | 2.5 | 2.5 | 2.5 | 4.0 | 4.0 | 4.0 |
| balance | | | | Water to 100 | | | |

(B.1): n-$C_{18}$-alkyl-$(OCH_2CH_2)_{25}$—OH
(B.2): $C_{10}$-$C_{18}$-alkylpolygycoside blend
(B.3): Sodium $C_{10}$-$C_{12}$-alkyl benzenesulfonate
(B.4): Sodium cumenesulfonate
(B.5): Sodium laurethsulfate - n-$C_{12}H_{25}$—O—$(CH_2CH_2O)_3$—$SO_3Na$
(B.6): n-$C_{12}H_{25}(CH_3)_2N{\rightarrow}O$
**for comparative tests without inventive compounds those were replaced by the same amount of diethylene glycol.

Lipase Activity:

Lipolase activity at certain points in time as indicated in Table 2 was be determined by employing pNitrophenol-valerate (2.4 mM pNP-C5 in 100 mM Tris pH 8.0, 0.01% Triton X100) as a substrate. The absorption was measured at 20° C. every 30 seconds over 5 minutes at 405 nm. The slope (absorbance increase at 405 nm per minute) of the time dependent absorption-curve is directly proportional to the activity of the lipase.

Table 2 displays lipase activity in liquid formulations measured after storage; 1-30 days at 37° C. The lipolytic activity values provided in Table 2 were calculated referring to the 100% value determined in the reference formulation at the time 0.

The nomenclature of formulations is as follows: the Roman number before the full stop characterizes the base formulation, the Arabian number the type of salt (A.# inventive salt (component (a)); C-(A.#) comparative compound). Zero ("0"): no salt, but diethylene glycol.

TABLE 2 lipase activity in the course of time of storage at 37° C.

| Formulation identifier | | | | | | | | | | |
|---|---|---|---|---|---|---|---|---|---|---|
| Base formulation | compound | T0 | 1 d | 3 d | 6 d | 10 d | 15 d | 20 d | 25 d | 30 d |
| I. | 0 | 95 | 89 | 77 | 68 | 53 | 38 | 30 | 22 | 16 |
| I. | (A.1) | 96 | 96 | 93 | 94 | 89 | 85 | 82 | 64 | 72 |
| I. | (A.3) | 101 | 100 | 98 | 95 | 91 | 88 | 85 | 68 | 78 |
| I. | (A.4) | 103 | 100 | 99 | 96 | 95 | 93 | 90 | 86 | 85 |
| I. | (A.6) | 97 | 96 | 94 | 92 | 89 | 85 | 80 | 78 | 75 |
| I. | (A.7) | 95 | 95 | 91 | 85 | 81 | 76 | 69 | 65 | 59 |
| I. | C-(A.15) | 97 | 95 | 80 | 67 | 55 | 41 | 32 | 22 | 20 |
| I. | C-(A.16) | 95 | 90 | 81 | 68 | 51 | 40 | 34 | 25 | 24 |
| I. | C-(A.17) | 97 | 90 | 80 | 70 | 53 | 42 | 38 | 33 | 29 |
| I. | C-(A.18) | 98 | 91 | 84 | 72 | 55 | 45 | 39 | 32 | 29 |
| II. | 0 | 94 | 92 | 81 | 73 | 57 | 41 | 32 | 25 | 20 |
| II. | (A.2) | 95 | 94 | 92 | 90 | 88 | 84 | 80 | 75 | 68 |
| II. | (A.5) | 102 | 100 | 97 | 95 | 93 | 89 | 86 | 72 | 79 |
| II. | (A.6) | 103 | 100 | 99 | 96 | 94 | 92 | 90 | 86 | 88 |
| II. | (A.8) | 96 | 94 | 90 | 85 | 80 | 80 | 76 | 72 | 68 |
| II. | (A.9) | 97 | 93 | 90 | 87 | 83 | 81 | 77 | 75 | 76 |
| II. | (A.10) | 96 | 96 | 92 | 89 | 83 | 84 | 79 | 76 | 73 |
| II. | (A.12) | 100 | 98 | 96 | 95 | 88 | 86 | 80 | 77 | 76 |
| II. | C-(A.15) | 96 | 95 | 82 | 65 | 56 | 40 | 33 | 26 | 22 |
| II. | C-(A.22) | 95 | 87 | 79 | 67 | 55 | 40 | 33 | 24 | 18 |
| III. | 0 | 96 | 93 | 83 | 74 | 63 | 51 | 42 | 30 | 24 |
| III. | (A.4) | 100 | 98 | 96 | 93 | 90 | 85 | 84 | 82 | 77 |
| III. | (A.6) | 104 | 100 | 101 | 97 | 94 | 90 | 89 | 86 | 82 |
| III. | (A.9) | 97 | 95 | 93 | 88 | 84 | 80 | 77 | 73 | 71 |
| III. | (A.10) | 96 | 96 | 91 | 86 | 82 | 79 | 76 | 73 | 69 |
| III. | (A.11) | 97 | 96 | 93 | 84 | 83 | 76 | 71 | 70 | 63 |
| III. | (A.12) | 102 | 98 | 97 | 95 | 91 | 86 | 80 | 78 | 74 |
| III. | C-(A.20) | 100 | 92 | 79 | 70 | 51 | 39 | 30 | 22 | 16 |
| III. | C-(A.21) | 101 | 93 | 78 | 68 | 50 | 39 | 31 | 25 | 20 |
| III. | C-(A.22) | 98 | 92 | 76 | 66 | 48 | 37 | 28 | 23 | 19 |
| IV. | 0 | 88 | 85 | 81 | 70 | 60 | 55 | 46 | 39 | 33 |
| IV. | (A.1) | 98 | 96 | 93 | 92 | 87 | 84 | 82 | 79 | 71 |
| IV. | (A.3) | 99 | 100 | 98 | 95 | 90 | 88 | 85 | 80 | 74 |
| IV. | (A.4) | 101 | 100 | 97 | 93 | 90 | 89 | 86 | 81 | 73 |
| IV. | (A.6) | 96 | 96 | 91 | 89 | 86 | 85 | 81 | 78 | 75 |
| IV. | (A.7) | 97 | 95 | 90 | 85 | 81 | 78 | 73 | 70 | 64 |
| IV. | C-(A.15) | 94 | 95 | 82 | 72 | 59 | 44 | 36 | 30 | 23 |
| IV. | C-(A.16) | 95 | 90 | 81 | 67 | 55 | 41 | 34 | 28 | 25 |
| IV. | C-(A.17) | 96 | 93 | 86 | 74 | 63 | 51 | 46 | 38 | 33 |
| IV. | C-(A.18) | 95 | 91 | 84 | 72 | 58 | 49 | 46 | 39 | 35 |
| V. | 0 | 83 | 80 | 75 | 68 | 59 | 50 | 41 | 36 | 30 |
| V. | (A.2) | 97 | 94 | 90 | 87 | 84 | 81 | 78 | 74 | 69 |
| V. | (A.4) | 101 | 98 | 94 | 90 | 87 | 84 | 80 | 76 | 71 |
| V. | (A.5) | 101 | 100 | 98 | 96 | 94 | 88 | 84 | 77 | 74 |
| V. | (A.7) | 96 | 95 | 92 | 88 | 84 | 80 | 75 | 70 | 66 |
| V. | (A.11) | 97 | 96 | 91 | 89 | 85 | 77 | 73 | 68 | 60 |
| V. | (A.13) | 95 | 96 | 91 | 87 | 80 | 70 | 61 | 52 | 45 |
| V. | C-(A.15) | 98 | 95 | 86 | 74 | 63 | 54 | 41 | 39 | 30 |
| V. | C-(A.16) | 96 | 92 | 85 | 70 | 65 | 58 | 49 | 37 | 28 |
| VI. | 0 | 82 | 79 | 72 | 63 | 54 | 47 | 38 | 30 | 25 |
| VI. | (A.4) | 102 | 99 | 96 | 91 | 86 | 82 | 80 | 75 | 65 |

TABLE 2-continued lipase activity in the course of time of storage at 37° C.

| Formulation identifier | | | | | | | | | | |
|---|---|---|---|---|---|---|---|---|---|---|
| Base formulation | compound | T0 | 1 d | 3 d | 6 d | 10 d | 15 d | 20 d | 25 d | 30 d |
| VI. | (A.5) | 99 | 97 | 95 | 91 | 83 | 78 | 73 | 70 | 63 |
| VI. | (A.6) | 96 | 90 | 87 | 84 | 81 | 74 | 70 | 67 | 61 |
| VI. | (A.11) | 97 | 92 | 88 | 84 | 83 | 78 | 75 | 72 | 65 |
| VI. | C-(A.18) | 96 | 90 | 83 | 75 | 58 | 50 | 48 | 37 | 32 |

Protease Activity:

Savinase activity at certain points in time as indicated in Table 3 was be determined by employing Succinyl-Ala-Ala-Pro-Phe-p-nitroanilide (Suc-AAPF-pNA, short AAPF) as substrate. pNA is cleaved from the substrate molecule by proteolytic cleavage, resulting in release of yellow color of free pNA which was determined by measuring $OD_{405}$. Measurement were done at 20° C.

Table 3 displays protease activity measured in liquid formulations after storage for 1 to 30 days at 37° C. The proteolytic activity values provided in Table 3 were calculated referring to the 100% value determined in the reference formulation at the time 0.

The nomenclature of formulations is as follows: the Roman number before the full stop characterizes the base formulation, the Arabian number the type of salt (A.# inventive salt (component (a)); C-(A.#) comparative compound). Zero ("0"): no salt, but diethylene glycol.

TABLE 3 protease activity in the course of time of storage at 37° C.

| Formulation identifier | | | | | | | | | | |
|---|---|---|---|---|---|---|---|---|---|---|
| Base formulation | compound | T0 | 1 d | 3 d | 6 d | 10 d | 15 d | 20 d | 25 d | 30 d |
| I. | 0 | 98 | 98 | 86 | 67 | 49 | 38 | 30 | 23 | 8 |
| I. | (A.1) | 96 | 94 | 91 | 75 | 59 | 48 | 42 | 36 | 29 |
| I. | (A.4) | 100 | 97 | 95 | 76 | 60 | 50 | 45 | 36 | 32 |
| I. | (A.5) | 99 | 96 | 94 | 73 | 58 | 49 | 44 | 38 | 33 |
| I. | (A.6) | 96 | 93 | 87 | 75 | 59 | 50 | 45 | 40 | 29 |
| I. | C-(A.15) | 98 | 92 | 85 | 64 | 47 | 39 | 31 | 22 | 8 |
| I. | C-(A.16) | 98 | 91 | 84 | 66 | 49 | 38 | 30 | 23 | 10 |
| I. | C-(A.17) | 98 | 90 | 81 | 70 | 49 | 38 | 30 | 23 | 12 |
| III. | 0 | 96 | 95 | 86 | 71 | 51 | 40 | 33 | 21 | 12 |
| III. | (A.6) | 92 | 96 | 92 | 82 | 69 | 59 | 50 | 41 | 34 |
| III. | (A.8) | 94 | 95 | 93 | 78 | 68 | 60 | 52 | 42 | 33 |
| III. | (A.12) | 96 | 96 | 92 | 80 | 70 | 61 | 50 | 39 | 31 |
| III. | C-(A.17) | 92 | 94 | 83 | 71 | 53 | 42 | 34 | 27 | 14 |
| III. | C-(A.18) | 94 | 94 | 85 | 72 | 54 | 43 | 35 | 28 | 14 |
| V. | 0 | 83 | 98 | 86 | 70 | 49 | 38 | 30 | 23 | 13 |
| V. | (A.1) | 84 | 93 | 88 | 80 | 62 | 54 | 46 | 38 | 30 |
| V. | (A.2) | 87 | 90 | 90 | 83 | 66 | 58 | 50 | 44 | 36 |
| V. | (A.6) | 88 | 91 | 89 | 84 | 70 | 60 | 52 | 43 | 35 |
| V. | C-(A.18) | 83 | 90 | 83 | 64 | 50 | 40 | 33 | 25 | 16 |
| VI. | 0 | 87 | 93 | 86 | 70 | 49 | 38 | 30 | 23 | 11 |
| VI. | (A.4) | 84 | 90 | 88 | 76 | 68 | 61 | 53 | 44 | 30 |
| VI. | (A.7) | 85 | 90 | 84 | 74 | 66 | 59 | 50 | 40 | 31 |
| VI. | (A.9) | 83 | 87 | 85 | 75 | 67 | 60 | 51 | 40 | 30 |
| VI. | (A.11) | 86 | 91 | 87 | 77 | 69 | 58 | 49 | 42 | 32 |
| VI. | C-(A.15) | 85 | 90 | 84 | 66 | 47 | 36 | 29 | 20 | 10 |

II.3 Textile Cleaning Tests

The detergent performance of formulations in cleaning two types of test fabrics was carried out. Testing cloth samples comprised a complex soil containing proteinaceous and fatty components due to CFT process as well as test cloth samples contained a fatty/particulate type of soil.

The test was performed as follows: a multi stain monitor containing 8 standardized soiled fabric patches, each of 2.5×2.5 cm size and stitched on two sides to a polyester carrier was washed together in a launder-O-meter with 2.5 g of cotton fabric and 5 g/L of the liquid test laundry detergent, Table 4.

The conditions were as follows: Device: Launder-0-Meter from SDL Atlas, Rock Hill, USA. Washing liquor: 250 ml, washing time: 60 minutes, washing temperature: 30° C. Water hardness: 2.5 mmol/L; Ca:Mg:HCO₃ 4:1:8

Fabric to liquor ratio 1:12 After the wash cycle, the multi stain monitors were rinsed in water, followed by drying at ambient temperature over a time period of 14 hours.

The following pre-soiled test fabrics were used:
CFT C-S-10: butter on cotton
CFT C-S-62: lard, colored on cotton
CFT C-S-68: chocolate ice-cream on cotton
EMPA 112: cocoa on cotton
EMPA 141/1: lipstick on cotton
EMPA 125: monitor for tensid
wfk20D: pigment and sebum-type fat on polyester/cotton mixed fabric
CFT C-S-70: chocolate mousse
wfk=wfk test fabrics GmbH, Krefeld
EMPA=Swiss Federal Institute of Materials Testing
CFT=Center for Test Material B.V.

The total level of cleaning was evaluated using color measurements. Reflectance values of the stains on the monitors were measured using a sphere reflectance spectrometer (SF 500 type from Datacolor, USA, wavelength range 360-700 nm, optical geometry d/8°) with a UV cutoff filter at 460 nm. In this case, with the aid of the CIE-Lab color space classification, the bright-ness L*, the value a* on the red-green color axis and the b* value on the yellow-blue color axis, were measured before and after washing and averaged for the 8 stains of the monitor. The change of the color value (Δ E) value, defined and calculated automatically by the evaluation color tools on the following equation:

$$\Delta E = \Delta \text{ Delta } a*2 + \Delta \text{ Delta } b*2 ++ \Delta \text{ Delta } L*2,$$

Δ E is a measure of the achieved cleaning effect. All measurements were repeated six times to yield an average number. Note that higher Δ E values show better cleaning. A difference of 1 unit can be detected by a skilled person. A non-expert can detect 2 units easily. The results are shown in Table 5

$R_w$=washed soil reflectance
$R_o$=unsoiled reflectance

The increase in detergency due to the builder was calculated as: A total of 6 replications of each cloth were run during this study; a statistical confidence level of 90-95% was calculated.

Test formulations were manufactured by making formulations VII to XIII by mixing the components according to Table 14.

The respective salt (component (a)) or comparative compound was added, if applicable, to the respective base formulation in amounts provided in Table 4.

Lipolase® 100 L was added, if applicable, to the respective base formulation in amounts provided in Table 4.

Savinase® 16.0 L was added, if applicable, to the respective base formulation in amounts provided in Table 4.

Water was added to accomplish the balance to 100.

TABLE 4 liquid laundry formulations

| Ingredients | Wt-% in formularion | | | | | | |
|---|---|---|---|---|---|---|---|
| | VII. | VIII. | IX. | X. | XI. | XII. | XIII. |
| Base formulation: | | | | | | | |
| (B.1) | 8 | 8 | 8 | 35 | 35 | 35 | 35 |
| (B.2) | 6 | 6 | 6 | — | — | — | — |
| (B.3) | 4 | 4 | 4 | 8 | 8 | 8 | 8 |
| (B.4) | — | — | — | 10 | 10 | 10 | 10 |
| (B.5) | 4 | 4 | 4 | 4 | 4 | 4 | 4 |
| (B.6) | 2.5 | 2.5 | 2.5 | — | — | — | — |
| Sorbitol | — | — | — | 2 | 2 | 2 | 2 |
| PEI-EO20 | 5 | 5 | 5 | 5 | 5 | 5 | 5 |
| Propyleneglycol | 4 | 4 | 4 | 8 | 8 | 8 | 8 |
| Glycerol | — | — | — | — | — | — | — |
| Ca-formiate | — | — | — | 2 | 2 | 2 | 2 |
| Additives: | | | | | | | |
| Savinase 16.0 L | — | — | — | — | — | 0.5 | 0.5 |
| Lipolase | — | — | 0.4 | — | 0.4 | 0.4 | 0.4 |
| component (a)** | — | 2.5 | 2.5 | — | 2.5 | 2.5 | 4 |
| balance | | | | Water to 100 | | | |

(B.1): n-$C_{18}$-alkyl-$(OCH_2CH_2)_{25}$—OH
(B.2): $C_{10}$-$C_{18}$-alkylpolygycoside blend
(B.3): Sodium $C_{10}$-$C_{12}$-alkyl benzenesulfonate
(B.4): Sodium cumenesulfonate
(B.5): Sodium laurethsulfate - n-$C_{12}H_{25}$—O—$(CH_2CH_2O)_3$—$SO_3Na$
(B.6): n-$C_{12}H_{25}(CH_3)_2N \to O$
**for comparative tests without inventive compounds those were replaced by the same amount of diethylene glycol.

The increase in detergency due to salt (component (a)) was calculated as: a total of 6 examples of each cloth were run during this study; a statistical confidence level of >90% was calculated. Table 5 shows the sum of ΔE of the above mentioned multi-stain monitor. The launder-O-meter tests were executed with freshly prepared formulation (to) and with storing at 37° C. during a 2-month storage temperature. As an approximation one week at 37° C. is equivalent to 3% weeks at 20° C.

TABLE 5

Results of launder-O-meter tests

| Formulation identifier | | ΔE | ΔE | ΔE | ΔE | ΔE | ΔE |
|---|---|---|---|---|---|---|---|
| Base formulation | compound | ΔE T0 | 1 week | 2 weeks | 4 weeks | 6 weeks | 8 weeks |
| VII. | 0 | 158 | 157 | 159 | 158 | 158 | 156 |
| VIII. | C-(A.21) | 161 | 160 | 159 | 158 | 160 | 159 |
| VIII. | (A.12) | 157 | 160 | 157 | 158 | 158 | 157 |
| VIII. | (A.4) | 162 | 163 | 161 | 163 | 161 | 161 |
| VIII. | (A.2) | 160 | 159 | 161 | 158 | 160 | 158 |
| IX. | 0 | 183 | 180 | 174 | 170 | 166 | 161 |
| IX. | (A.2) | 184 | 183 | 180 | 178 | 177 | 173 |
| IX. | (A.3) | 183 | 184 | 181 | 179 | 179 | 175 |
| IX. | (A.4) | 185 | 185 | 183 | 181 | 182 | 181 |
| IX. | (A.7) | 181 | 179 | 180 | 178 | 179 | 177 |
| X. | 0 | 164 | 164 | 163 | 162 | 163 | 163 |
| XI. | 0 | 188 | 186 | 180 | 174 | 169 | 164 |
| XI. | (A.5) | 191 | 189 | 188 | 188 | 184 | 185 |
| XI. | (A.10) | 185 | 187 | 187 | 185 | 182 | 180 |
| XI. | (A.12) | 185 | 186 | 186 | 187 | 185 | 185 |
| XII. | 0 | 190 | 186 | 181 | 178 | 172 | 164 |
| XII. | (A.12) | 190 | 189 | 188 | 188 | 188 | 184 |
| XII. | (A.2) | 191 | 189 | 186 | 186 | 184 | 182 |
| XII. | (A.5) | 191 | 194 | 193 | 191 | 189 | 188 |
| XIII. | 0 | 194 | 190 | 184 | 177 | 171 | 165 |
| XIII. | C-(A.15) | 190 | 189 | 185 | 175 | 168 | 163 |
| XIII. | (A.8) | 191 | 191 | 189 | 189 | 186 | 186 |
| XIII. | (A.10) | 192 | 188 | 189 | 188 | 185 | 183 |
| XIII. | (A.12) | 190 | 191 | 190 | 188 | 187 | 188 |

The invention claimed is:

1. A liquid enzyme preparation containing component (a): at least one salt according to general formula (I)

$$(R^2)_3N^+\text{—}(CH_2)_n C(R^3)(R^4)\text{—}(O\text{—}X)_m\text{—}O\text{—}C(O)\text{—}R^1 A^- \qquad (I)$$

wherein
n is selected from 1 to 12,
m is zero,
$R^1$ is selected from the group consisting of methyl, ethyl, —CH(OH)—CH(OH)—COOH, CH(OH)—$CH_3$, (E)-CH═CHCOOH, (Z)—CH═CHCOOH, —$C_6H_5$, para-HO—$C_6H_4$—, o,p-dihydroxyphenyl, and 3,4,5-triyhydroxyphenyl, or —O—C(O)—$R^1$ together constitute a citrate,
$R^2$ are same or different and selected from $C_1$-$C_{10}$-alkyl and phenyl,
$R^3$ and $R^4$ are same or different and selected from hydrogen and $C_1$-$C_4$-alkyl,
X is $C_2$-$C_4$-alkylen, and
$A^-$ is an inorganic or organic counteranion,
component (b): at least one enzyme selected from hydrolases (EC 3),
and
optionally component (c): at least one compound selected from enzyme stabilizers different from component (a), preservatives, and surfactants.

2. The liquid enzyme preparation according to claim 1 wherein component (a) has a counterion selected from the group consisting of halide, sulphate, carbonate, tartrate, citrate, lactate, and methanesulfonate.

3. The liquid enzyme preparation according to claim 1 wherein $R^2$ in compound according to general formula (I) are all methyl.

4. The liquid enzyme preparation according to claim 1 wherein said enzyme preparation contains component (a) in amounts in the range of 0.1 to 30% by weight relative to the total weight of the enzyme preparation.

5. The liquid enzyme preparation according to claim 1 wherein component (a) contains as impurity a compound (a'):

$$(R^2)_3N^+\text{—}(CH_2)_n C(R^3)(R^4)\text{—}(O\text{—}X)_m\text{—}OHR^1\text{—}COO\text{—} \qquad (a')$$

wherein the variables $R^1$, $R^2$, X, n and m are the same as in the corresponding component (a).

6. The liquid enzyme preparation according to claim 1 wherein the enzyme preparation contains component (c), wherein component (c) comprises at least one enzyme stabilizer selected from the group consisting of boron-containing compounds and peptide aldehydes.

7. A method of making a detergent formulation, the method comprising mixing the liquid enzyme preparation of claim 1 in one or more steps with one or more detergent components.

8. The liquid enzyme preparation of claim 1, wherein the component (b) is selected from the group consisting of lipases (EC 3.1.1), endopeptidases (EC 3.4.21), triacylglycerol lipase (EC 3.1.1.3), and subtilisin type proteases (EC 3.4.21.62).

9. The liquid enzyme preparation of claim 1, wherein the surfactants are selected from the group consisting of non-ionic, amphoteric, and anionic surfactants.

10. A process for making an enzyme preparation, said process comprising the steps of mixing at least
component (a): at least one salt that is a compound of general formula (I),

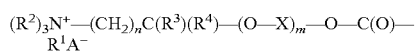
(I)

wherein
n is selected from 1 to 12,
m is zero,
$R^1$ is selected from the group consisting of methyl, ethyl, —CH(OH)—CH(OH)—COOH, CH(OH)—CH$_3$, (E)-CH=CHCOOH, (Z)—CH=CHCOOH, —C$_6$H$_5$, para-HO—C$_6$H$_4$—, o,p-dihydroxyphenyl, and 3,4,5-triydroxyphenyl, or —O—C(O)—$R^1$ together constitute a citrate,
$R^2$ are same or different and selected from $C_1$-$C_{10}$-alkyl, phenyl,
$R^3$ and $R^4$ are same or different and selected from hydrogen and $C_1$-$C_4$-alkyl,
X is $C_2$-$C_4$-alkylen, and
$A^-$ is a counteranion, inorganic or organic
and
component (b): at least one enzyme selected from hydrolases (EC 3).

11. The process of claim 10, wherein the component (b) is selected from the group consisting of lipases (EC 3.1.1), endopeptidases (EC 3.4.21), triacylglycerol lipase (EC 3.1.1.3), and subtilisin type proteases (EC 3.4.21.62).

12. A method of stabilizing at least one enzyme selected from hydrolases (EC 3) within a liquid enzyme preparation by the step of adding at least one salt of the general formula (I),

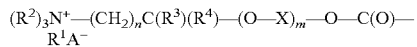
(I)

wherein
n is selected from 1 to 12,
m is zero,
$R^1$ is selected from the group consisting of methyl, ethyl, —CH(OH)—CH(OH)—COOH, CH(OH)—CH$_3$, (E)-CH=CHCOOH, (Z)—CH=CHCOOH, —C$_6$H$_5$, para-HO—C$_6$H$_4$—, o,p-dihydroxyphenyl, and 3,4,5-triydroxyphenyl, or —O—C(O)—$R^1$ together constitute a citrate,
$R^2$ are same or different and selected from $C_1$-$C_{10}$-alkyl, phenyl,
$R^3$ and $R^4$ are same or different and selected from hydrogen and $C_1$-$C_4$-alkyl,
X is $C_2$-$C_4$-alkylen, and
$A^-$ is a counteranion, inorganic or organic.

13. The method according to claim 12, wherein the enzyme is stabilized in the presence of at least one surfactant.

14. A method of using at least one salt of the general formula (I),

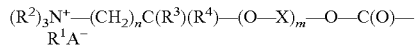
(I)

wherein
n is selected from 1 to 12,
m is zero,
$R^1$ is selected from the group consisting of methyl, ethyl, —CH(OH)—CH(OH)—COOH, CH(OH)—CH$_3$, (E)-CH=CHCOOH, (Z)—CH=CHCOOH, —C$_6$H$_5$, para-HO—C$_6$H$_4$—, o,p-dihydroxyphenyl, and 3,4,5-triydroxyphenyl, or —O—C(O)—$R^1$ together constitute a citrate,
$R^2$ are same or different and selected from $C_1$-$C_{10}$-alkyl, phenyl,
$R^3$ and $R^4$ are same or different and selected from hydrogen and $C_1$-$C_4$-alkyl,
X is $C_2$-$C_4$-alkylen, and
$A^-$ is a counteranion, inorganic or organic,
the method comprising using the salt of the general formula (I) as an additive for at least one enzyme selected from hydrolases (EC 3), wherein said salt and said enzyme are solid and wherein stabilization of said enzyme occurs when said salt and said enzyme are contacted with at least one solvent.

15. A liquid detergent formulation comprising
component (a): at least one salt according to general formula (I)

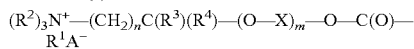
(I)

wherein
n is selected from 1 to 12,
m is zero,
$R^1$ is selected from the group consisting of methyl, ethyl, —CH(OH)—CH(OH)—COOH, CH(OH)—CH$_3$, (E)-CH=CHCOOH, (Z)—CH=CHCOOH, —C$_6$H$_5$, para-HO—C$_6$H$_4$—, o,p-dihydroxyphenyl, and 3,4,5-triydroxyphenyl, or —O—C(O)—$R^1$ together constitute a citrate,
$R^2$ are same or different and selected from $C_1$-$C_{10}$-alkyl, phenyl,
$R^3$ and $R^4$ are same or different and selected from hydrogen and $C_1$-$C_4$-alkyl,
X is $C_2$-$C_4$-alkylen, and
$A^-$ is an inorganic or organic counteranion,
component (b): at least one enzyme selected from hydrolases (EC 3),
optionally component (c): at least one enzyme stabilizers different from component (a), and
at least one detergent component.

16. A method for removing stains comprising fat, comprising the step of contacting the stain with a detergent formulation according to claim 15, wherein at least one enzyme comprised in component (b) of the detergent formulation comprises at least one lipase (EC 3.1.1).

17. The method according to claim 16, wherein the stain is to be removed from a textile at a temperature ≤40° C.

18. The method of claim 16, wherein the at least one enzyme comprised in component (b) of the detergent formulation comprises at least one triacylglycerol lipase (EC 3.1.1.3).

19. The detergent formulation of claim 15, wherein the component (b) is selected from the group consisting of lipases (EC 3.1.1), endopeptidases (EC 3.4.21), triacylglycerol lipase (EC 3.1.1.3), and subtilisin type proteases (EC 3.4.21.62).

20. The detergent formulation of claim 15, wherein the component (c) is selected from the group consisting of boron containing compounds, phenyl boronic acid (PBA) or its derivatives, and 4-formyl phenyl boronic acid (4-FPBA).

* * * * *